US012746017B2

(12) United States Patent
Iorgulescu et al.

(10) Patent No.: US 12,746,017 B2
(45) Date of Patent: Sep. 29, 2026

(54) ANTI-SKIVING GUIDE TUBE AND SURGICAL SYSTEM INCLUDING THE SAME

(71) Applicant: MAKO Surgical Corp., Weston, FL (US)

(72) Inventors: Radu Iorgulescu, Boca Raton, FL (US); Amir A. Sharifi-Mehr, Bloomingdale, NJ (US)

(73) Assignee: MAKO Surgical Corp., Weston, FL (US)

( * ) Notice: Subject to any disclaimer, the term of this patent is extended or adjusted under 35 U.S.C. 154(b) by 22 days.

(21) Appl. No.: 18/609,403

(22) Filed: Mar. 19, 2024

(65) Prior Publication Data

US 2024/0315710 A1 Sep. 26, 2024

Related U.S. Application Data

(60) Provisional application No. 63/454,346, filed on Mar. 24, 2023.

(51) Int. Cl.

*A61B 17/17* (2006.01)
*A61B 17/34* (2006.01)
(Continued)

(52) U.S. Cl.

CPC .......... *A61B 17/1757* (2013.01); *A61B 34/30* (2016.02); *A61B 2017/00477* (2013.01); (Continued)

(58) Field of Classification Search

CPC ........ A61B 2017/3454; A61B 17/1633; A61B 2017/00858; A61B 2017/3484

See application file for complete search history.

(56) References Cited

U.S. PATENT DOCUMENTS

| | | | |
|---|---|---|---|
| 4,527,637 | A | 7/1985 | Bodine |
| 4,615,400 | A | 10/1986 | Bodine |

(Continued)

FOREIGN PATENT DOCUMENTS

| | | | |
|---|---|---|---|
| EP | 3827760 | A1 | 6/2021 |
| WO | 2022040305 | A1 | 2/2022 |

OTHER PUBLICATIONS

International Search Report for Application No. PCT/US2024/020843 dated Jul. 8, 2024, 2 pages.

*Primary Examiner* — David W Bates
(74) *Attorney, Agent, or Firm* — Howard & Howard Attorneys PLLC

(57) ABSTRACT

A surgical system to facilitate a spinal procedure on a vertebral body includes a robotic manipulator including an arm and a tool holder. The tool holder defines a tool holder channel extending along a tool holder axis. The tool holder channel has a tool holder diameter. The surgical system also includes a guide tube configured to slide into the tool holder channel. The guide tube includes a body extending along a body axis and defining a body channel. The body has a proximal portion defining the body channel and having an outer proximal portion diameter that is less than or equal to the tool holder. The body has a distal portion extending from the proximal portion along the body axis and further defining the body channel. The distal portion includes a side surface that is configured to engage a surface of the vertebral body to minimize skiving.

29 Claims, 14 Drawing Sheets

(51) Int. Cl.
*A61B 34/30* (2016.01)
*A61B 17/00* (2006.01)
*A61B 17/56* (2006.01)

(52) U.S. Cl.
CPC ............... *A61B 2017/00858* (2013.01); *A61B 2017/3484* (2013.01); *A61B 2017/564* (2013.01)

(56) References Cited

U.S. PATENT DOCUMENTS 4,618,296 A 10/1986 Allaire et al.
4,869,625 A 9/1989 Stone
6,019,767 A * 2/2000 Howell .............. A61B 17/1714 606/88
6,106,539 A * 8/2000 Fortier ............... A61B 17/3417 604/164.06
8,010,180 B2 8/2011 Quaid et al.
8,469,963 B2 * 6/2013 Shoham ................. A61B 17/17 604/164.09
8,852,222 B2 10/2014 O'Sullivan
8,960,337 B2 2/2015 Hall et al.
9,008,757 B2 4/2015 Wu
9,119,655 B2 9/2015 Bowling et al.
9,393,057 B2 7/2016 MacMillan et al.
9,592,562 B2 3/2017 Harif
9,603,665 B2 3/2017 Bowling et al.
9,639,156 B2 5/2017 Iorgulescu et al.
9,707,043 B2 7/2017 Bozung
10,357,257 B2 7/2019 Kostrzewski
10,357,324 B2 7/2019 Flatt et al.
11,014,173 B2 5/2021 Huijs et al.
11,033,341 B2 6/2021 Kang et al.
11,337,766 B2 5/2022 Elbanna et al.
11,510,740 B2 11/2022 Breisacher et al.
11,701,090 B2 7/2023 Moctezuma De La Barrera et al.
2004/0143281 A1 * 7/2004 Hart ................... A61B 17/3496 606/185
2007/0255282 A1 * 11/2007 Simonton .......... A61B 17/3472 606/60
2007/0260184 A1 * 11/2007 Justis ..................... A61B 17/16 604/164.01
2010/0076478 A1 * 3/2010 Smith .................. A61B 90/361 606/185
2010/0286695 A1 * 11/2010 Hannani ............ A61B 17/1671 606/86 A
2011/0144590 A1 * 6/2011 Sakai, Jr. ........... A61B 17/3421 604/164.01
2011/0152866 A1 * 6/2011 Knutson ............ A61B 17/3472 606/86 R
2011/0257672 A1 * 10/2011 Friedman ........... A61B 17/3421 606/190
2011/0288553 A1 * 11/2011 Jansen ............... A61B 17/1637 606/83
2012/0041454 A1 * 2/2012 Johnstone .......... A61B 17/0401 606/139
2012/0165851 A1 * 6/2012 Murakami ................ B24B 5/02 451/28
2016/0008011 A1 1/2016 Kostrzewski
2016/0038018 A1 * 2/2016 Wilson ............... A61B 1/00154 600/114
2016/0081753 A1 3/2016 Kostrzewski
2016/0270815 A1 * 9/2016 Mazur ................ A61B 17/0218
2016/0317239 A1 * 11/2016 Turner ................... A61B 90/10
2016/0324616 A1 * 11/2016 Zenz-Olson ....... A61B 17/3468
2017/0224358 A1 * 8/2017 Kostrzewski .......... A61B 34/30
2018/0256174 A1 * 9/2018 Deeny ................ A61B 17/1615
2018/0311748 A1 11/2018 Novovic et al.
2018/0344351 A1 * 12/2018 Begg .................. A61B 17/3417
2019/0350596 A1 11/2019 Kostrzewski
2020/0281608 A1 9/2020 Sharifi-Mehr et al.
2020/0305898 A1 * 10/2020 Arai ................... A61B 17/1631
2021/0100567 A1 * 4/2021 Sharifi-Mehr ..... A61B 17/3496
2021/0121186 A1 * 4/2021 Mincieli ................ A61B 90/06
2022/0233251 A1 7/2022 Bowling et al.
2022/0266364 A1 8/2022 Hoss
2022/0313280 A1 * 10/2022 Sarendranath ..... A61B 17/1631
2022/0409299 A1 * 12/2022 Bush, Jr. ................ A61B 34/10
2024/0008933 A1 1/2024 Stawiaski et al.
2025/0213255 A1 * 7/2025 Cannestra .............. A61B 17/16

* cited by examiner

FIG. 7
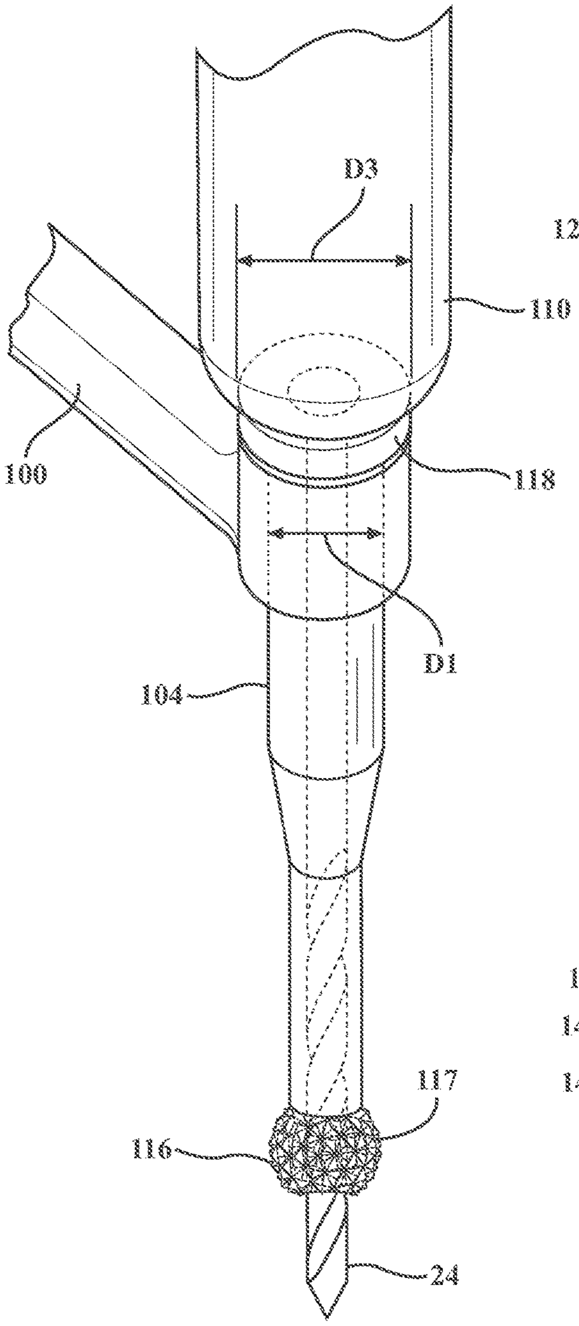
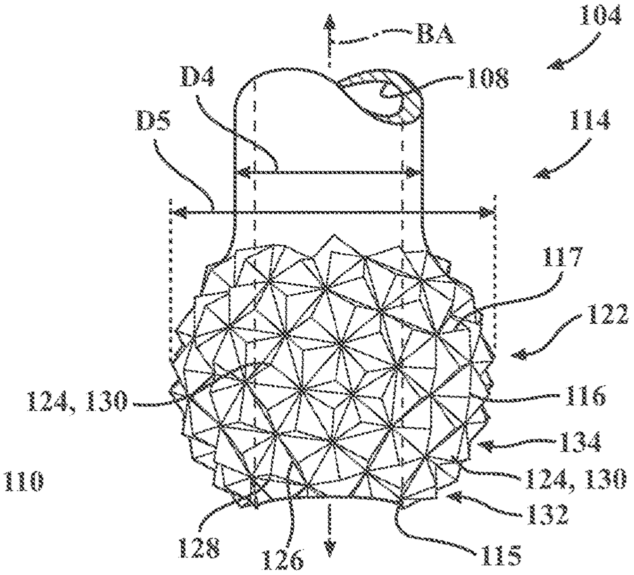
FIG. 8
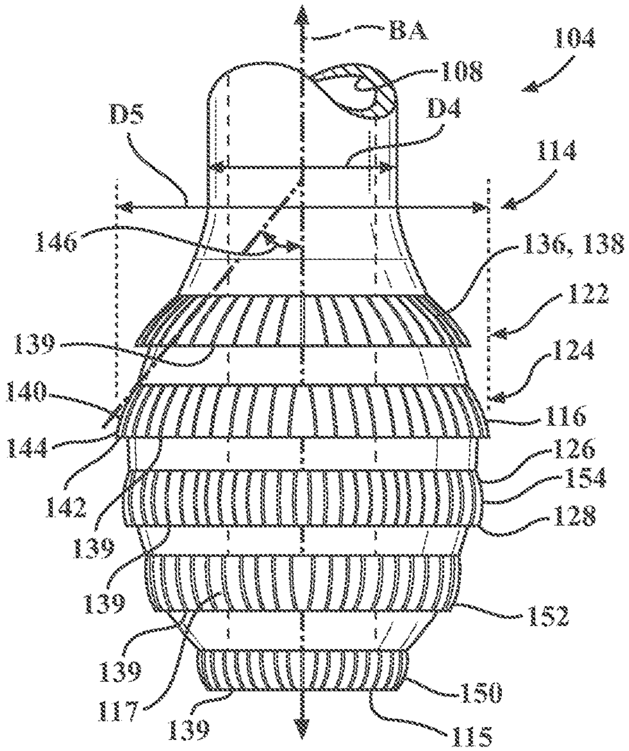
FIG. 9

ANTI-SKIVING GUIDE TUBE AND SURGICAL SYSTEM INCLUDING THE SAME

CROSS-REFERENCE TO RELATED APPLICATIONS

This application claims priority to and all benefits of U.S. Provisional Patent Application No. 63/454,346, filed Mar. 24, 2023, which is incorporated herein by reference in its entirety.

BACKGROUND

Robotic systems for performing surgical spinal procedures are known. For instance, robotic systems are currently utilized to place pedicle screws in a patient's spine. Robotics have also been used to provide a guide that is aligned with a planned trajectory associated with the target vertebra. Such guides are used by the surgeon to insert tools within the guide along the planned trajectory. For example, the surgeon may insert a cannula in the guide for creating passage the target vertebra through the tissue. A drill can be inserted in the cannula to create a pilot hole in the pedicle along the target trajectory. A screwdriver can be inserted in the cannula to drive the pedicle screw into the target vertebra. Conventional cannulas used for this purpose typically provide limited features to facilitate engagement between the cannula and the surface of the target vertebra. For example, conventional cannulas typically include a few teeth that are axially oriented relative to the cannula and pointed down at the tip of the cannula (without any side engaging features). Yet, the surface of the bone, particularly, the pedicle entry point of the vertebra, is a complex surface. Surgical workflows involving such tools are often subjected to inaccuracy due, in part, to skiving of the tools relative to the complex surface of the vertebral body. Skiving is an error condition whereby the tool moves in an unexpected or undesirable direction relative to the bone surface, which results in inaccuracies related to the function of the tool. For example, as the conventional cannula is inserted into the guide, the cannula is susceptible to skiving at the entry point of the pedicle due to its limited engagement features. Misalignment issues can occur, for example, if the teeth of the cannula engage the bone at surface that is not flat or if the cannula teeth engage the bone from an angle.

SUMMARY

This Summary introduces a selection of concepts in a simplified form that are further described below in the Detailed Description below. This Summary is not intended to limit the scope of the claimed subject matter nor identify key features or essential features of the claimed subject matter.

A first aspect of the disclosure involves a surgical system to facilitate a surgical procedure, such as a spinal procedure, on a bone, such as a vertebral body, the surgical system comprising: a robotic manipulator comprising an arm and a tool holder coupled to the arm, wherein the tool holder defines a tool holder channel extending along a tool holder axis, and wherein the tool holder channel has a tool holder diameter; and a guide tube configured to slide into the tool holder channel and comprising, a body extending along a body axis and defining a body channel that is configured to receive a surgical tool, wherein the body has a proximal portion defining the body channel and having an outer proximal portion diameter that is less than or equal to the tool holder diameter such that the proximal portion is slidable into the tool holder channel to align the body with the tool holder, and wherein the body has a distal portion extending from the proximal portion along the body axis and further defining the body channel; wherein the distal portion comprises a side surface disposed about the body axis, and wherein the side surface comprises abrasive features extending away from the body axis and configured to engage a surface of the bone to minimize skiving.

A second aspect of the disclosure involves a guide tube of a surgical system, the surgical system being configured to facilitate surgical procedure, such as a spinal procedure, on a bone, such as a vertebral body, and the surgical system including a robotic manipulator including an arm and a tool holder coupled to the arm, with the tool holder defining a tool holder channel extending along a tool holder axis, and with the tool holder channel having a tool holder diameter, the guide tube comprising: a body extending along a body axis and defining a body channel that is configured to receive a surgical tool, wherein the body has a proximal portion defining the body channel and having an outer proximal portion diameter that is configured to be less than or equal to the tool holder diameter such that the proximal portion is configured to be slidable into the tool holder channel to align the body with the tool holder, and wherein the body has a distal portion extending from the proximal portion along the body axis and further defining the body channel; and wherein the distal portion comprises a side surface disposed about the body axis, and wherein the side surface comprises abrasive features extending away from the body axis and configured to engage a surface of the bone to minimize skiving.

A third aspect of the disclosure involves a method of operating a surgical system to facilitate a surgical procedure, such as a spinal procedure, on a bone, such as a vertebral body, the surgical system including a robotic manipulator comprising an arm and a tool holder coupled to the arm, wherein the tool holder defines a tool holder channel extending along a tool holder axis and the tool holder channel defining a tool holder diameter; a guide tube including a body extending along a body axis and defining a body channel that is configured to receive a surgical tool, wherein the body has a proximal portion defining the body channel and having an outer proximal portion diameter that is less than or equal to the tool holder diameter, and the body has a distal portion extending from the proximal portion along the body axis and further defining the body channel, and the distal portion of the body includes a side surface disposed about the body axis and comprising abrasive features extending away from the body axis, the method comprising the steps of: controlling the robotic manipulator to align the tool holder such that the tool holder axis is aligned with a target axis defined relative to the bone; inserting the guide tube in the tool holder for aligning the body axis of the guide tube with the target axis; and engaging the surface of the bone with the side surface of the distal portion to minimize skiving of the guide tube relative to the surface of the bone.

A fourth aspect of the disclosure involves a surgical system comprising: a robotic manipulator comprising an arm and a tool holder coupled to the arm, wherein the tool holder defines a tool holder channel; and a guide tube configured to freely slide relative to the tool holder channel and comprising, a body defining a body channel that is configured to receive a surgical tool therethrough, wherein the body has a distal portion comprising side surface comprising abrasive features.

A fifth aspect of the disclosure involves a surgical system comprising: a robotic manipulator comprising an arm and a tool holder coupled to the arm, wherein the tool holder defines a tool holder channel; a surgical tool; and a guide tube configured to freely slide relative to the tool holder channel and being separated from the surgical tool, the guide tube comprising a body defining a channel that is configured to receive the surgical tool therethrough such that the surgical tool is configured to freely slide relative to the guide tube, wherein the body has a distal portion comprising a side surface disposed about the body axis and comprising abrasive features extending away from the body axis.

Any of the aspects can be combined, in part, or in whole. Any of the aspects can be combined, in part, or in whole, with any of the following implementations:

In some implementations, the robotic manipulator is configured to align the tool holder such that the tool holder axis is aligned with a target axis defined relative to the vertebral body, and wherein the body axis of the guide tube is aligned with the target axis when the guide tube is inserted into the tool holder channel.

In some implementations, the guide tube is configured to be passively supported by the tool holder. In some implementations, the guide tube to passively engage the bone surface. In some implementations, the guide tube is freely slidable along the tool holder axis. In some implementations, the tool holder and the guide tube are integral with one another. In some implementations, the tool holder and the guide tube selectively attachable with one another.

In some implementations, the surgical tool is separated from, and freely slidable relative to, the guide tube. In some implementations, the surgical tool is may be selectively attached to the guide tube. In some implementations, the surgical tool may be any one or more of a tap, awl, probe, drill, screwdriver, or any other suitable surgical tool.

In some implementations, the proximal portion has a proximal flange having a flange outer diameter greater than the tool holder diameter, and wherein the proximal flange is configured to be placed above an upper surface of the tool holder.

In some implementations, the abrasive features of the side surface are disposed 360 degrees about the body axis. In some implementations, the abrasive features of the side surface are further defined as a plurality of protrusions. In some implementations, at least a portion of the plurality of protrusions are oriented to face downward with respect to the body axis toward the distal end. In some implementations, the distal portion includes a bulbous portion, and wherein the bulbous portion comprises the side surface comprising the abrasive features. In some implementations, the bulbous portion comprises the plurality of protrusions. In some implementations, the bulbous portion may have a spherical or hemispherical configuration.

In some implementations, at least a portion of the plurality of protrusions are oriented to face downward with respect to the body axis toward the distal end. In some implementations, each protrusion of the plurality of protrusions is of the same geometry. In some implementations, the protrusions of the plurality of protrusions have varying geometries. In some implementations, the plurality of protrusions is disposed 360 degrees about the body axis. In some implementations, a geometry of at least one protrusion is a pyramid, prism, cone, wire, or prong. In some implementations, each protrusion has a protrusion base and a protrusion tip extending from the protrusion base away from the body axis. In some implementations, the plurality of protrusions has a helical configuration with respect to the body axis.

In some implementations, the plurality of protrusions comprises layers of flanges disposed annularly about the body axis. In some implementations, each flange of the layers of flanges comprises a first flange surface extending away from the body axis and a second flange surface extending away from the body axis, and wherein the first and second flange surfaces terminate at a flange edge that is configured to engage the vertebral body to minimize skiving. In some implementations, the first flange surface is obliquely oriented with respect to the body axis. In some implementations, at least one layer of the layers of flanges overlaps another layer of the layers of flanges with respect to the body axis.

In some implementations, the proximal portion has a proximal flange having a flange outer diameter configured to be greater than the tool holder diameter such that the proximal flange is configured to be placed above an upper surface of the tool holder, wherein the distal portion has a distal outer diameter that is less than the flange outer diameter, and wherein the bulbous portion has an outer bulbous diameter that is greater than or equal to the distal outer diameter.

In some implementations, the method further comprises, after controlling the robotic manipulator to align the tool holder such that the tool holder axis is aligned with the target axis, the step of inserting the guide tube through a patient incision until the side surface of the distal portion engages the surface of the vertebral body. In some implementations, the method further comprises, after engaging the surface of the vertebral body with the side surface of the distal portion, inserting the surgical tool in the body channel of the guide tube.

BRIEF DESCRIPTION OF THE DRAWINGS

Other advantages of the present disclosure will be readily appreciated, as the same becomes better understood by reference to the following detailed description when considered in connection with the accompanying drawings.

FIG. 7 is a perspective view including the guide tube of FIG. 6, with the surgical tool being disposed in the body channel of the body of the guide tube and the guide tube being disposed in the tool holder channel.

FIG. 8 is a side view of the distal portion of the guide tube having the side surface of the example of FIG. 6.

FIG. 9 is a side view of another implementation of the distal portion of the guide tube.

DETAILED DESCRIPTION

I. Example System Overview

With reference to the Figures, wherein like numerals indicate like or corresponding parts throughout the several views, a surgical system 10 (hereinafter "system") and method for operating the system 10 are described herein and shown throughout the accompanying Figures.

Figure 1:
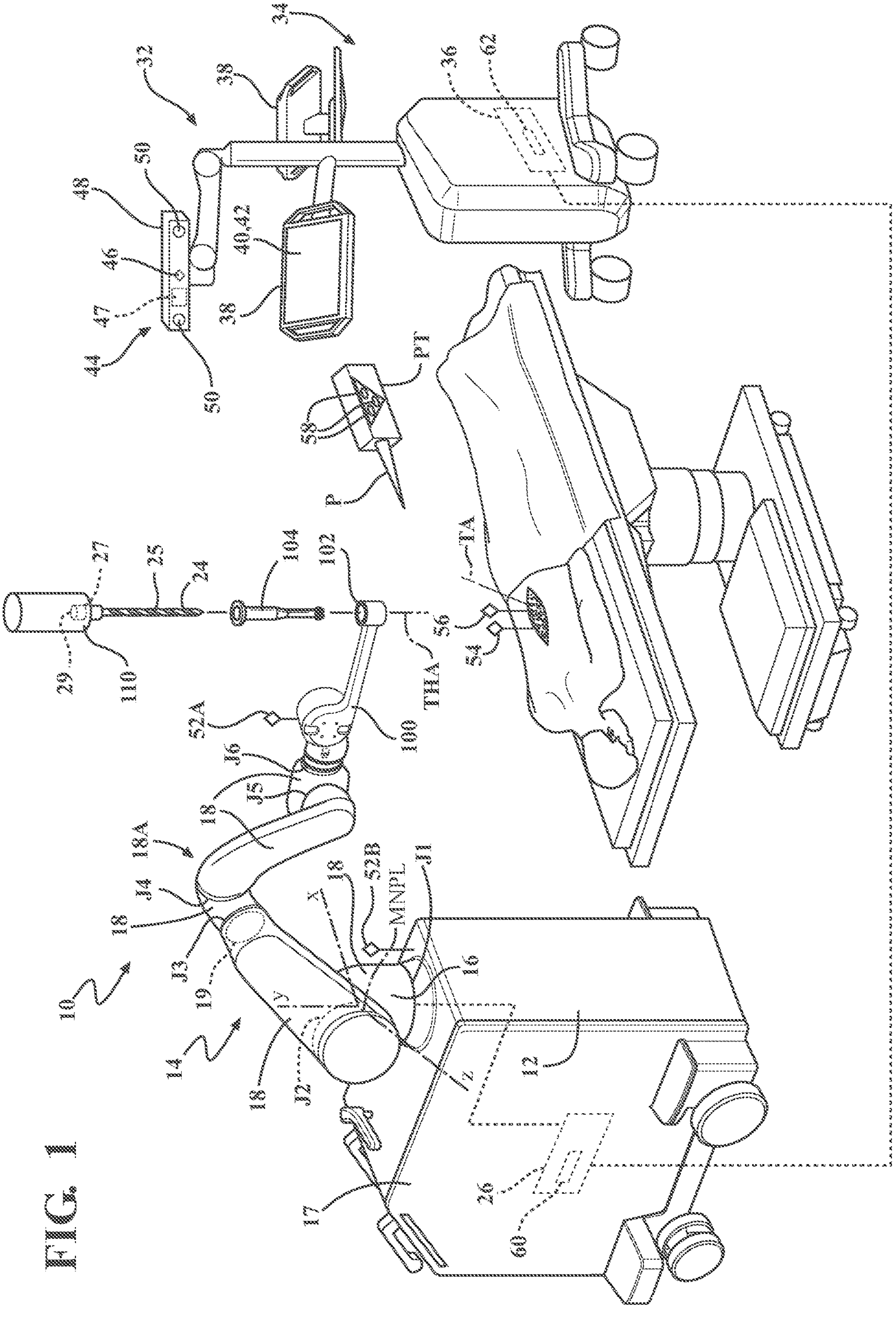
FIG. 1 is a perspective view of a surgical system including a robotic manipulator including an arm and a tool holder, according to one implementation.

As shown in FIG. 1, the system 10 is a robotic surgical system for treating an anatomy (surgical site) of a patient 12, such as bone or soft tissue. In FIG. 1, the patient 12 is undergoing a surgical procedure. The anatomy in FIG. 1 includes a spine of the patient 12. The surgical procedure may involve tissue removal or treatment. In one aspect, the surgical procedure may involve planning and executing of cannulation of tissue and insertion of an implant within one or more bone structures. In one example, as primarily described herein, the bone structure is a vertebra of the spine. The techniques and advantages described herein, however are not limited only to vertebral bodies, and may be utilized for treating any bone structure. Such bones may, for example, be in the limbs of the patient, and may include a distal or proximal femur, tibia, humerus, scapula, acetabulum, skull, ankle, or any other bone structure not described herein. The implant can be a pedicle screw when the bone structure is a vertebra. However, other types of implants are contemplated, and the disclosure is not limited solely to spinal surgery. The robotic system, according to one aspect, is configured to prepare the anatomy for insertion of pedicle screws. Robotic systems, tools, and techniques for preparing for and installing pedicle screws can be like those described in U.S. patent application Ser. No. 16/184,376, filed Nov. 8, 2018, entitled "Robotic Spine Surgery System and Methods," the entire contents of which are hereby incorporated by reference.

The system 10 includes a manipulator 14, which may also be referred to as a robotic manipulator. In one example, the manipulator 14 has a base 16 and plurality of links 18. The plurality of links 18 may be commonly referred to as an arm 18A. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. The manipulator 14 may also be table mounted or gantry mounted. In other examples, more than one manipulator 14 may be utilized in a multiple arm configuration. The manipulator 14 comprises a plurality of joints (J) and a plurality of joint encoders 19 located at the joints (J) for determining position data of the joints (J). For simplicity, one joint encoder 19 is illustrated in FIG. 1, although it is to be appreciated that the other joint encoders 19 may be similarly illustrated. The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J). In one example, each of the joints (J) of the manipulator 14 are actively driven. In other examples, some joints (J) may be passively driven while other joints (J) are actively driven. For example, active joints (J) may support a passive mechanism located at the distal end of the arm 18A. The passive mechanism can be manually moved by the operator and mechanically constrained according to certain degrees of freedom, such as constrained only move in a plane, or a line.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference point, which does not move in the manipulator coordinate system MNPL. The manipulator 14 and/or manipulator cart 17 house a manipulator computer 26, or other type of control unit.

With continued reference to FIG. 1, the system 10 includes a tool holder 100 coupled to the arm 18A. The manipulator 14 is configured to move the tool holder 100 relative to the base 16 to interact with the anatomy. In one example, the tool holder 100 attaches to a distal flange of the manipulator 14. The tool holder 100 may be attached to the distal flange using fasteners, or using a clamping mechanism, such as described in U.S. Pat. No. 10,357,324, entitled, "Sterile Barrier Assembly, Mounting System, and Method for Coupling Surgical Components", the entire contents of which are hereby incorporated by reference. The tool holder 100 may be grasped by the operator to direct movement of the manipulator 14.

In some implementations, the manipulator 14 could be hand-held such that the base 16 would be defined by a base portion of a tool (e.g., a portion held free-hand by the user against the force of gravity) with the tool holder 100 being movable relative to the base portion via a system of actuators. In this example, the base portion has a reference coordinate system that is tracked, and the tool holder 100 has a coordinate system that is computed relative to the reference coordinate system (e.g., via motor and/or joint encoders and forward kinematic calculations). The user can move the base portion to a gross location relative to the anatomy, and movement of the tool holder 100 can be automatically controlled to be constrained by or align to a haptic object or trajectory. One example of this type of hand-held manipulator 14 can be implemented using aspects of the device described in U.S. Pat. No. 9,707,043, entitled "Surgical Instrument Including Housing, A Cutting Accessory that Extends from the Housing and Actuators that Establish the Position of the Cutting Accessory Relative to the Housing," the disclosure of which is hereby incorporated by reference in its entirety.

Figure 3:
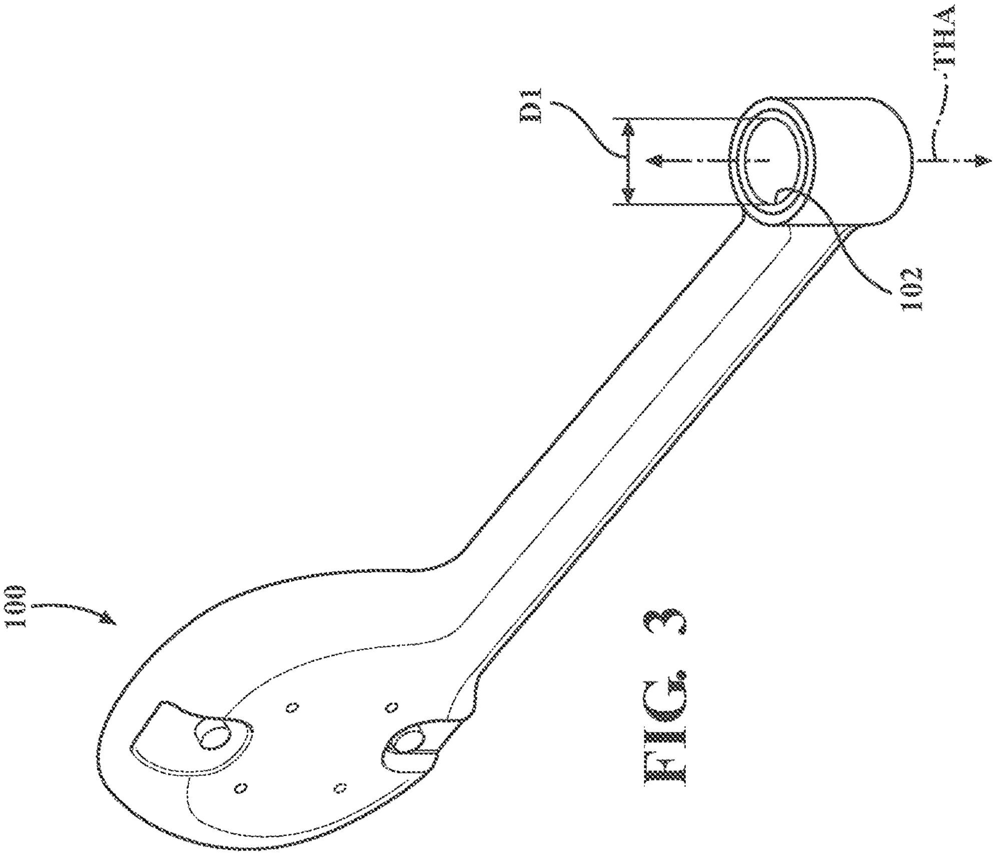
FIG. 3 is a perspective view of the tool holder defining a tool holder channel extending along a tool holder axis, according to one implementation.

With reference to FIG. 3, the tool holder 100 defines a tool holder channel 102 extending along a tool holder axis THA. The tool holder channel 100 has a tool holder diameter D1. The diameter D1 may be constant or variable along the tool holder channel 102. As will be described in the following section, a guide tube 104 is insertable within the tool holder channel 102.

As shown in FIG. 1, a surgical tool 110, such as a tap, awl, probe, drill, screwdriver, or any other suitable surgical tool, is configured to be inserted into the tool holder channel 102, and more specifically, inserted into the guide tube 104, when the guide tube 104 is inserted into the tool holder channel 102. The surgical tool 110 includes an energy applicator 24 designed to contact, or facilitate engagement with, the tissue of the patient 12 at the surgical site. In some configurations, the energy applicator 24 is an accessory that can releasably attach to the surgical tool 110. In alternative configurations, the energy applicator 24 is integrated with the surgical tool 110 such that they are part of a common device. For at least this reason, descriptions of the surgical tool 110 herein may apply fully to the energy applicator 24, and vice-versa, depending on the configuration of the surgical tool 110 and energy applicator 24. For surgical procedures involving entry point creation and cannulation, the energy applicator 24 is may be a rotary tool, such as a drill or bur. The energy applicator 24 may be rotatable about a tool axis. The surgical tool 110 can include a tool shaft 25, as shown in FIG. 1. A proximal end of the tool shaft 25 can be connected to a tool driver 27 that is driven by a tool motor 29, wherein the tool driver 27 and tool motor 29 are optionally included within a body of the surgical tool 110, as shown in FIG. 1, for example.

As shown in FIG. 1, the system 10 may further include a navigation system 32. The navigation system 32 is configured to track movement of various objects. Such objects include, for example, the manipulator 14, the tool holder 100, guide tube 104, the surgical tool 110, and/or the anatomy, e.g., certain vertebrae of the patient. The navigation system 32 tracks these objects to gather state information of one or more of the objects with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. Input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, head-mounted devices, and the like.

The navigation system 32 is configured to depict a visual representation of the anatomy and the tool holder 100, guide tube 104, and/or surgical tool 110 for visual guidance of any of the techniques described. The visual representation may be real (camera) images, virtual representations (e.g., computer models), or any combination thereof. The visual representation can be presented on any display viewable to the surgeon, such as the displays 38 of the navigation system 32, head mounted devices, or the like. The representations may be augmented reality, mixed reality, or virtual reality.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50. The camera unit 46 may include a camera controller 47 in communication with the optical sensors 50 to receive signals from the optical sensors 40. One example of an optical navigation system 32 is described in U.S. Pat. No. 9,008,757, filed on Sep. 24, 2013, entitled, "Navigation System Including Optical and Non-Optical Sensors," hereby incorporated by reference.

The navigation system 32 may include one or more trackers. In one example, the trackers may include a pointer tracker PT, one or more manipulator trackers 52, and one or more patient trackers 54, 56. In the illustrated example of FIG. 1, the one or more manipulator trackers 52 may be attached to any suitable component of the manipulator 14 or components attached to the manipulator. For example, the manipulator tracker 52 may be attached to the base 16 of the manipulator 14, any of the links 18 of the manipulator 14, the tool holder 100, the guide tube 104, and/or surgical tool 110 (i.e., tracker 52A). A patient tracker 54 may be firmly affixed to a vertebra of the patient 12, and the second patient tracker 56 is firmly affixed to pelvis of the patient 12 or to another vertebra. In this example, the patient trackers 54, 56 are firmly affixed to sections of bone. The pointer tracker PT may be firmly affixed to a pointer P, which can be used for registering the anatomy to the localizer coordinate system LCLZ. When present, the trackers 52, 54, 56, PT may be fixed to their respective components in any suitable manner.

The localizer 44 tracks the trackers 52, 54, 56 to determine a state of one or more of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

When optical localization is utilized, one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

Although one example of the navigation system 32 is shown, the navigation system 32 may have any other suitable configuration for tracking any of the described surgical objects. The illustrated tracker configuration is provided merely as one example for tracking objects within the operating space. Any number of trackers may be utilized and may be located in positions or on objects other than shown. In other examples, such as described below, the localizer 44 may detect objects absent any trackers affixed to objects.

In one example, the navigation system 32 and/or localizer 44 are ultrasound-based. For example, the navigation system 32 may comprise an ultrasound imaging device coupled to the navigation computer 36. The ultrasound imaging device may be robotically controlled or may be hand-held. The ultrasound imaging device images any of the aforementioned objects, e.g., the manipulator 14 and the patient 12, and generates state signals to the navigation system 32 based on the ultrasound images. The ultrasound images may be of any ultrasound imaging modality. The navigation computer 36 may process the images in near real-time to determine states of the objects. Ultrasound tracking can be performed absent the use of trackers affixed to the objects being tracked. The ultrasound imaging device may have any suitable configuration and may be different than the camera unit 46 as shown in FIG. 1. One example of an ultrasound tracking system can be like that described in U.S. patent application Ser. No. 15/999,152, filed Aug. 16, 2018, entitled "Ultrasound Bone Registration With Learning-Based Segmentation And Sound Speed Calibration," the entire contents of which are incorporated by reference herein.

In another example, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the navigation system 32 based on RF signals received from the RF emitters. The navigation computer 36 and/or the navigation system 32 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electromagnetic tracker, inductive tracker, or the like. The trackers may be passive or actively energized. The EM transceiver generates an EM field and generates state signals to the navigation system 32 based upon EM signals received from the trackers. The navigation computer 36 and/or the navigation system 32 may analyze the received EM signals to associate relative states thereto. Again, such navigation system 32 examples may have structural configurations that are different than the navigation system 32 configuration as shown throughout the Figures.

In yet another example, the navigation system 32 and/or localizer 44 utilize a machine vision system which includes a video camera coupled to the navigation computer 36. The video camera is configured to locate a physical object in a target space. The physical object has a geometry represented by virtual object data stored by the navigation computer 36. The detected objects may be tools, obstacles, anatomical features, trackers, or the like. The video camera and navigation computer 36 are configured to detect the physical objects using image processing techniques such as pattern, color, or shape recognition, edge detection, pixel analysis, neutral net or deep learning processing, optical character recognition, barcode detection, or the like. The navigation computer 36 can compare the captured images to the virtual object data to identify and track the objects. A tracker may or may not be coupled to the physical object. If trackers are utilized, the machine vision system may also include infrared detectors for tracking the trackers and comparing tracking data to machine vision data. Again, such navigation system 32 examples may have structural configurations that are different than the navigation system 32 configuration as shown throughout the Figures. Examples of machine vision tracking systems can be like that described in U.S. Pat. No. 9,603,665, entitled "Systems and Methods for Establishing Virtual Constraint Boundaries" and/or like that described in U.S. Provisional Patent Application No. 62/698,502, filed Jul. 16, 2018, entitled "Systems and Method for Image Based Registration and Calibration," the entire contents of which are incorporated by reference herein.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

Figure 2:
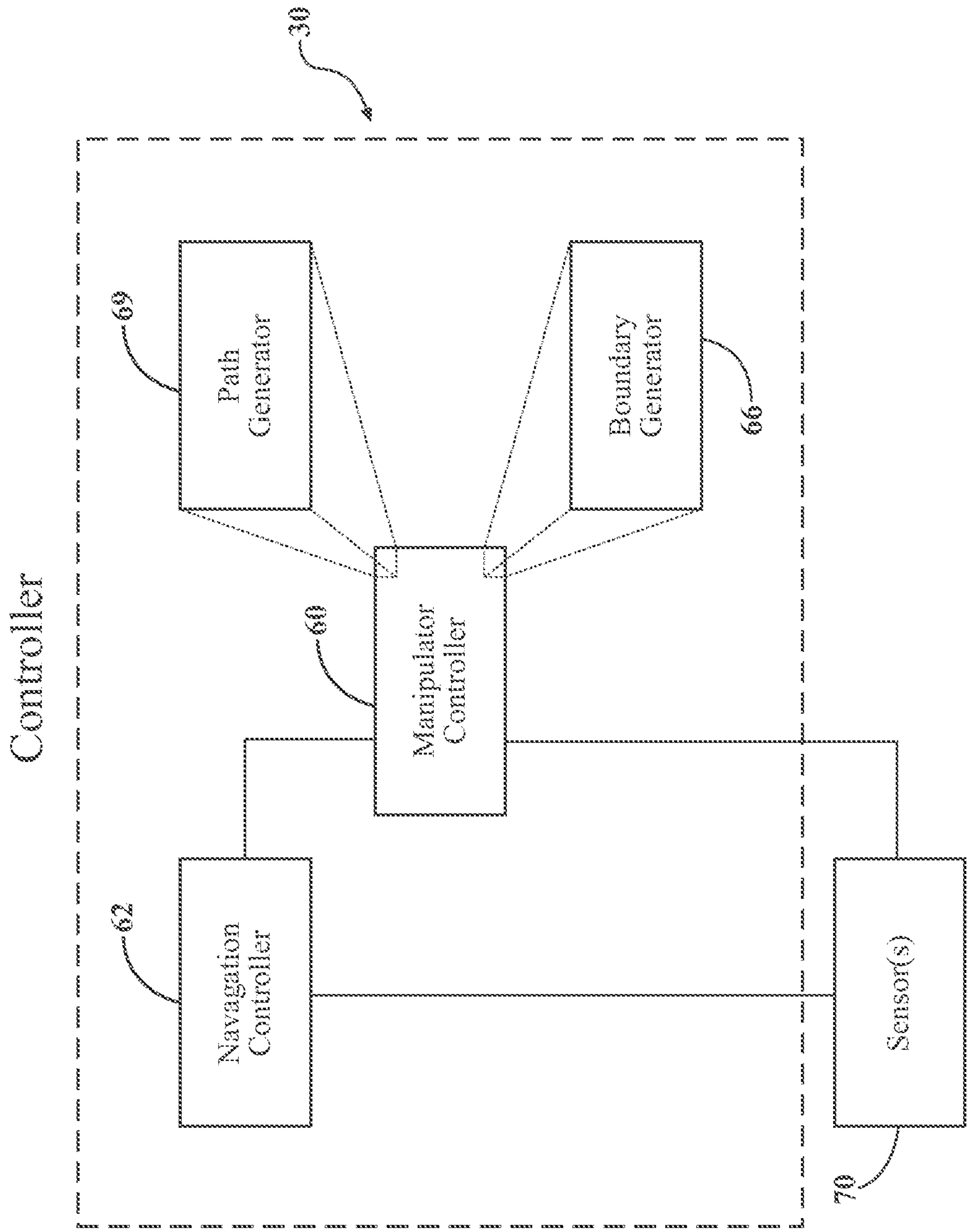
FIG. 2 is a block diagram of controllers of the robotic surgical system, according to one implementation.

Referring to FIG. 2, the system 10 includes one or more controllers 30 (hereinafter referred to as "controller"). The controller 30 includes software and/or hardware for controlling the manipulator 14 and navigation system 32. The controller 30 directs the motion of the manipulator 14 and controls a state (position and/or orientation) of the tool holder 100 with respect to the patient.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include instructions stored in one or more non-transitory computer readable medium or memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the manipulator 14. In one example, as shown in FIG. 1, the manipulator controller 60 is implemented on the manipulator computer 26. The manipulator controller 60 may receive and process data from a single source or multiple sources. The controller 30 further includes a navigation controller 62 for communicating the state data relating to the anatomy to the manipulator 14 to the manipulator controller 60. The manipulator controller 60 receives and processes the state data provided by the navigation controller 62 to direct movement of the manipulator 14. In one example, as shown in FIG. 1, the navigation controller 62 is implemented on the navigation computer 36. The manipulator controller 60 or navigation controller 62 may also communicate states of the patient 12 and manipulator 14 to the operator by displaying an image of the anatomy and the manipulator 14 on the one or more displays 38. The manipulator computer 26 or navigation computer 36 may also command display of instructions or request information using the display 38 to interact with the operator and for directing the manipulator 14.

The one or more controllers 30, including the manipulator controller 60 and navigation controller 62, may be implemented on any suitable device or devices in the system 10, including, but not limited to, the manipulator computer 26, the navigation computer 36, and any combination thereof. As will be described herein, the controller 30 is not limited to one controller, but may include a plurality of controllers for various systems, components or sub-systems of the surgical system 10. These controllers may be in communication with each other (e.g., directly or indirectly), and/or with other components of the surgical system 10, such as via physical electrical connections (e.g., a tethered wire harness) and/or via one or more types of wireless communication (e.g., with a WiFi™ network, Bluetooth®, a radio network, and the like). Any of the one or more controllers 30 may be realized as or with various arrangements of computers, processors, control units, and the like, and may comprise discrete components or may be integrated (e.g., sharing hardware, software, inputs, outputs, and the like). Any of the one or more controllers may implement their respective functionality using hardware-only, software-only, or a combination of hardware and software. Examples of hardware include, but is not limited, single or multi-core processors, CPUs, GPUs, integrated circuits, microchips, or ASICs, digital signal processors, microcontrollers, field programmable gate arrays, systems on a chip, discrete circuitry, and/or other suitable hardware, and the like. The one or more controllers may implement software programs, software modules, algorithms, logical rules, look-up tables and other reference data, and various software layers for implementing any of the capabilities described herein. Equivalents of the software and hardware for the one or more controllers 30, and peripheral devices connected thereto, are fully contemplated.

As shown in FIG. 2, the controller 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual boundaries (VB) for constraining the tool holder 100, guide tube 104, and/or surgical tool 110. Such virtual boundaries (VB) may also be referred to as virtual meshes, virtual constraints, line haptics, or the like. The virtual boundaries (VB) may be defined with respect to a 3-D bone model registered to the one or more patient trackers 54, 56 such that the virtual boundaries (VB) are fixed relative to the bone model. The state of the tool holder 100 is tracked relative to the virtual boundaries (VB). In one example, the state of the tool holder 100 is measured relative to the virtual boundaries (VB) for purposes of determining when and where haptic feedback force is applied to the manipulator 14, or more specifically, the tool holder 100.

In one example, the virtual boundary (VB) may be a virtual target axis TA that is defined relative to and registered to the anatomy using the navigation system 32. The target axis TA can be determined based on pre-operative or intra-operative surgical planning for inserting pedicle screw into the vertebral body. The target axis TA can be implemented as a virtual line to which the tool holder 100 can be virtually constrained. In other implementations, the target axis TA can include a virtual cylinder. The manipulator 14 may be triggered to attract the tool holder 100 to the target axis TA in response to a user input (e.g., foot pedal) or in response to the tool holder 100 reaching an attraction zone adjacent the target axis TA. Examples of attractive haptics that can be used to guide the tool holder 100 to the target axis TA can be like that described in U.S. Patent App. Pub. No. US 2022/0233251, entitled "Systems and Methods for Guiding Movement of a Tool", the contents of which are hereby incorporated by reference. The user apply force to the tool holder 100 to pull the tool holder 100 off the target axis. In examples in which more than one target axis TA is planned, the system 10 may selectively activate or deactivate a target axis TA depending on the location of the tool holder 100 using haptic techniques, such as those described in U.S. Patent No. U.S. Pat. No. 9,639,156, entitled "Systems and Methods for Selectively Activating Haptic Guide Zones", the contents of which are hereby incorporated by reference.

Optionally, a tool path generator 69 is another software module run by the controller 30, and more specifically, the manipulator controller 60. The tool path generator 69 may generate a path for the tool holder 100, guide tube 104, and/or surgical tool 110 to traverse, such as for removing sections of the anatomy to receive an implant. One exemplary system and method for generating the tool path is explained in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries (VB) and/or tool paths may be generated offline rather than on the manipulator computer 26 or navigation computer 36. Thereafter, the virtual boundaries (VB) and/or tool paths may be utilized at runtime by the manipulator controller 60.

Additionally, it may be desirable to control the manipulator 14 in different modes of operation for the system 10.

For example, the system 10 may enable the manipulator 14 to interact with the site using manual and automated modes of operation. Examples of these modes can be like that described in U.S. Pat. No. 9,119,655, entitled, "Surgical Manipulator Capable of Controlling a Surgical Instrument in Multiple Modes," the disclosure of which is hereby incorporated by reference. In the automated mode, the manipulator 14 directs movement of the tool holder 100 relative to the surgical site. In one instance, the controller 30 models the tool holder 100 as a virtual rigid body and determines forces and torques to apply to the virtual rigid body to advance and constrain the tool holder 100 along any trajectory or path in the automated mode. Movement of the tool 20 in the automated mode is constrained in relation to the virtual constraints generated by the boundary generator 66 and/or path generator 69.

In the automated mode, the manipulator 14 is capable of moving the tool holder 100 free of operator assistance. Free of operator assistance may mean that an operator does not physically move the tool holder 100 by applying external force to move the tool holder 100. Instead, the operator may use some form of control to manage starting and stopping of movement. For example, the operator may hold down a button of a control to start movement of the tool holder 100 and release the button to stop movement of the tool holder 100. Alternatively, the operator may press a button to start movement of the tool holder 100 and press a button to stop motorized movement of the tool holder 100 along the trajectory or path. The manipulator 14 uses motorized movement to advance the tool holder 100 in accordance to pre-planned parameters.

Alternatively, the system 10 may be operated in the manual mode. Here, in one instance, the operator manually directs, and the manipulator 14 controls, movement of the tool holder 100 at the surgical site. The operator physically contacts the tool holder 100 to cause movement of the tool holder 100. The manipulator 14 may monitor the forces and torques placed on the tool holder 100 by the operator in order to position the tool holder. A sensor system that is part of the manipulator 14, such as a force-torque transducer, or electrical current sensors at the joint motors, measures these external forces and torques applied to the manipulator 14 and/or holder 100, e.g., in six degrees of freedom. In one example, the sensor is coupled between the distal-most link of the manipulator (J6) and the end effector. In response to the applied forces and torques, the one or more controllers 30, 60, 62 are configured to determine a commanded position of the tool holder 100 by evaluating the forces/torques applied externally to the tool holder 100 with respect to virtual model of the tool holder 100 in a virtual simulation. The manipulator 14 then mechanically moves the tool holder 100 to the commanded position in a manner that emulates the movement that would have occurred based on the forces and torques applied externally by the operator. Movement of the tool holder 100 in the manual mode is also constrained in relation to the virtual constraints generated by the boundary generator 66 and/or path generator 69.

The above-described automated mode and manual mode may be implemented as part of an admittance-type robotic system, whereby the system controls a position of the tool holder 100 in response to force input. Alternatively, the robotic system may implement the automated mode and manual modes as part of an impedance-type robotic system, whereby the system controls a force to move the tool holder 100 in response to positional changes of the tool holder 100. Other modes that are contemplated with the impedance-type robotic system include an approach mode, haptic mode, free mode, input mode, or hold mode, as described in U.S. Patent No. U.S. Pat. No. 8,010,180, entitled "Haptic Guidance System and Method", the contents of which are hereby incorporated by reference.

II. Anti-Skiving Guide Tube

Figure 4:
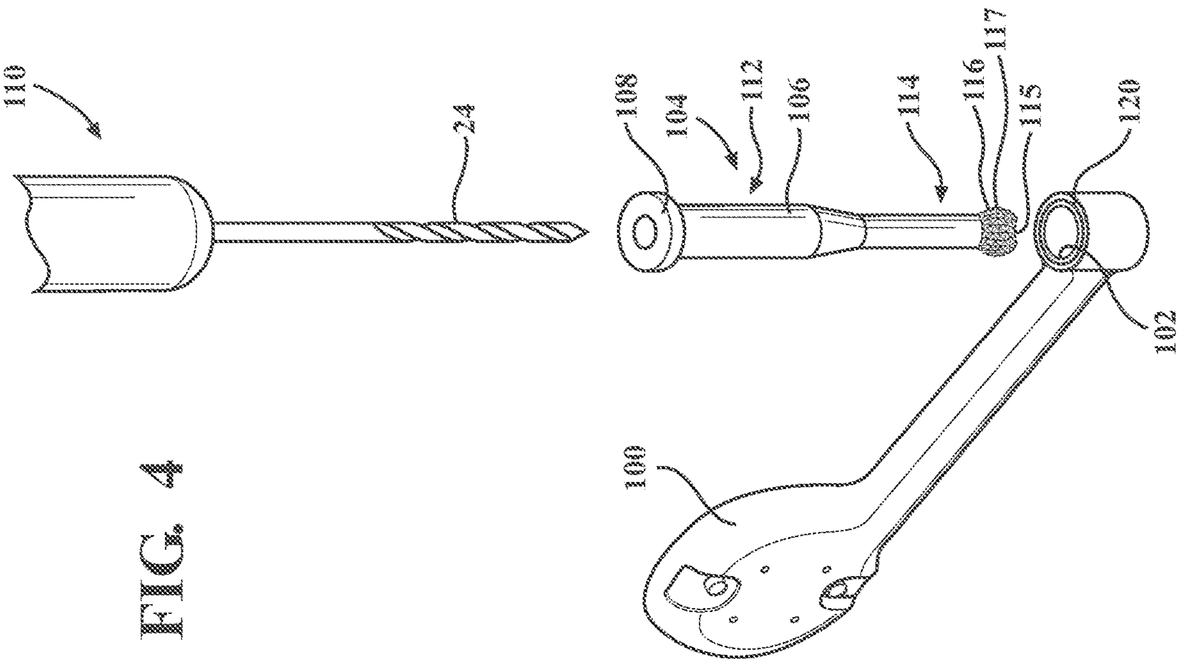
FIG. 4 is a perspective view of the tool holder, a guide tube configured to slide into the tool holder channel and with the guide tube having a body extending along a body axis and defining a body channel, and a surgical tool configured to be received by the body channel of the body of the guide tube, according to one implementation.
Figure 6:
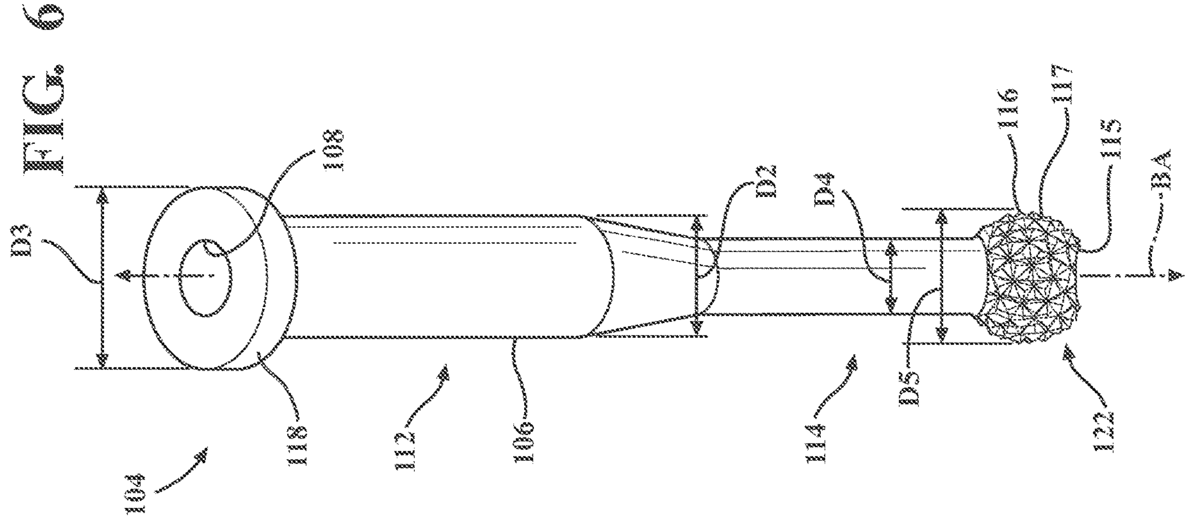
FIG. 6 is a perspective view of the guide tube including one example implementation of the side surface.
Figure 5:
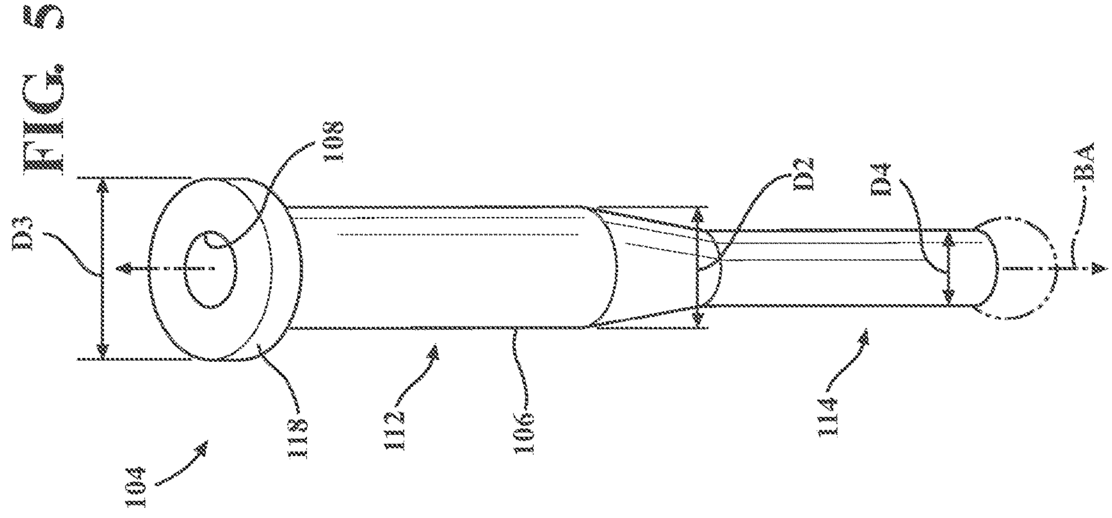
FIG. 5 is perspective view of the guide tube according to one implementation, with the body of the guide tube having a proximal portion defining the body channel and a distal portion extending from the proximal portion along the body axis and further defining the body channel, and with the distal portion including a side surface including abrasive features that are configured to engage a surface of a vertebral body to minimize skiving.

With reference to FIG. 4, the system 10 also includes a guide tube 104 configured to slide into the tool holder 100, and more specifically, into the tool holder channel 102. As shown in FIGS. 5 and 6, the guide tube 104 includes a body 106 extending along a body axis BA. The body 106 defines a body channel 108 that is configured to receive the surgical tool 110 therethrough. To this end, the body 106 may be understood as being a cannulated structure. The body 106 also has a proximal portion 112 defining the body channel 108 and having an outer proximal portion diameter D2 that is less than or equal to the tool holder diameter D1 such that the proximal portion 112 is slidable into the tool holder channel 102 to align the body 106 with the tool holder 100. In one implementation, the proximal portion 112 smooth In one example, the difference between diameter D1 and D2 is less than 1 mm, to provide a tight fit between the inner surface of the tool holder channel 102 and the outer surface of the guide tube 104.

The guide tube 104 is configured to be passively supported by the tool holder 100. The guide tube 104 is configured to freely slide into and out of the tool holder channel 102 without requiring a mechanical connection, such as threading, or clamping. Alternatively, the guide tube 104 may be configured to mechanically couple to the tool holder channel 102 using any suitable connection. The guide tube 104 can also be annularly symmetric such that the guide tube 104 can freely rotate with the tool holder channel 102 to any rotational position. However, if desired, the guide tube 106 and/or the tool holder channel 102 may have keying or orientation limiting features, such as slots, to limit insertion of the guide tube 104 relative to one or more rotational positions relative to the tool holder channel 102. The guide tube 104 may be used to guide insertion of various components, such as the energy applicator 24 of the surgical tool 110. The guide tube 104 may be used for any other suitable application where components require guidance into the patient and/or any suitable application where trajectory assistance is desired.

The body 106 also has a distal portion 114 extending from the proximal portion 112 along the body axis BA and further defining the body channel 108. The distal portion 114 is fixed to the body 106. The distal portion 114 and the proximal portion 112 may be separate components (i.e., two pieces) or the distal portion 114 and the proximal portion 112 may be integral with one another (i.e., one piece).

The distal portion 114 includes a side surface 116 having abrasive features 117 that are configured to engage a surface of the anatomical target. The side surface 116 may face away from the body axis BA. In other words, the abrasive features 117 may project from the side surface 116 transverse to the body axis BA. The side surface 116 engages a bone, such as a vertebral body, knee, hip, or any other suitable bone of a patient, to provide a stable resting position relative to the bone and hence minimize skiving of the guide tube 104 relative to the surface of the bone. However, the side surface 116 is not an actively driven component that is designed to remove material from the bone. For example, the side surface 116 is not actively rotated to function as a cutting bur. Instead, the side surface 116 is designed to passively interact with the bone surface. Various embodiments of the outer abrasive surface 116 are described in further detail below.

Figure 19A:
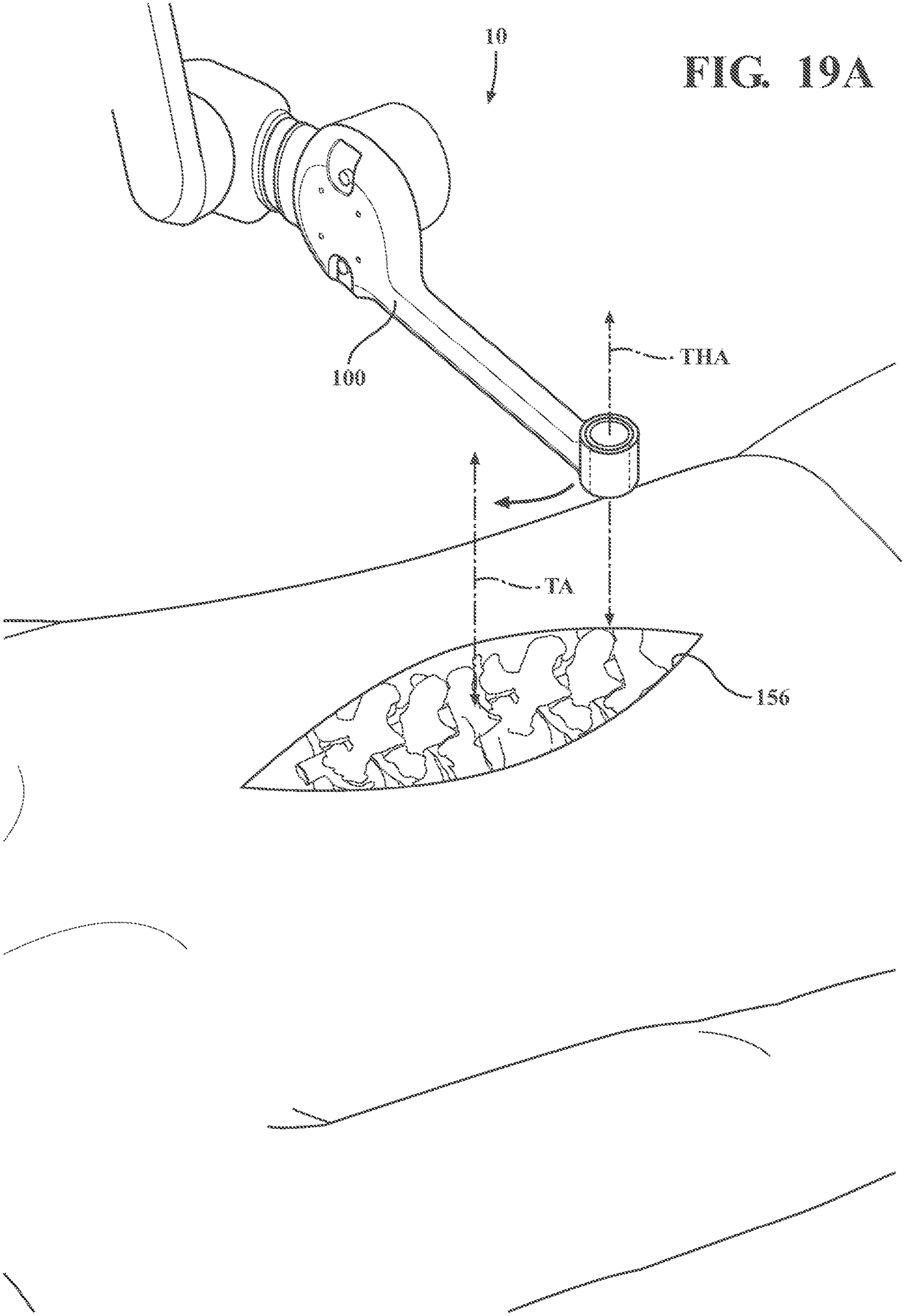
FIG. 19A is a perspective view of the tool holder and a vertebral body of a patient, with the tool holder axis and a target axis of the vertebral body being misaligned.
Figure 19B:
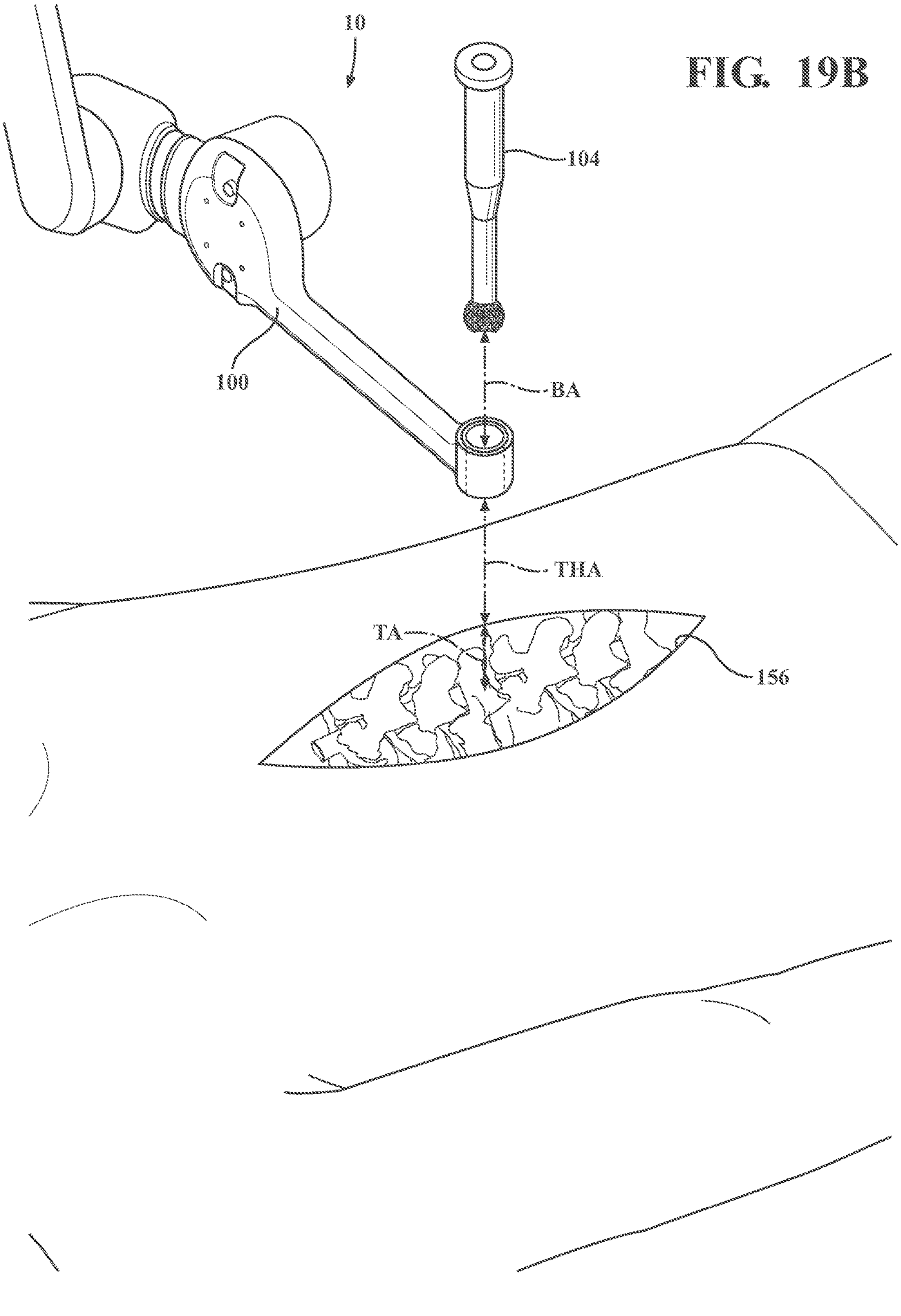
FIG. 19B is a perspective view of the tool holder and guide tube disposed above the vertebral body of the patient, with the tool holder axis and the target axis being aligned with one another.
Figure 19C:
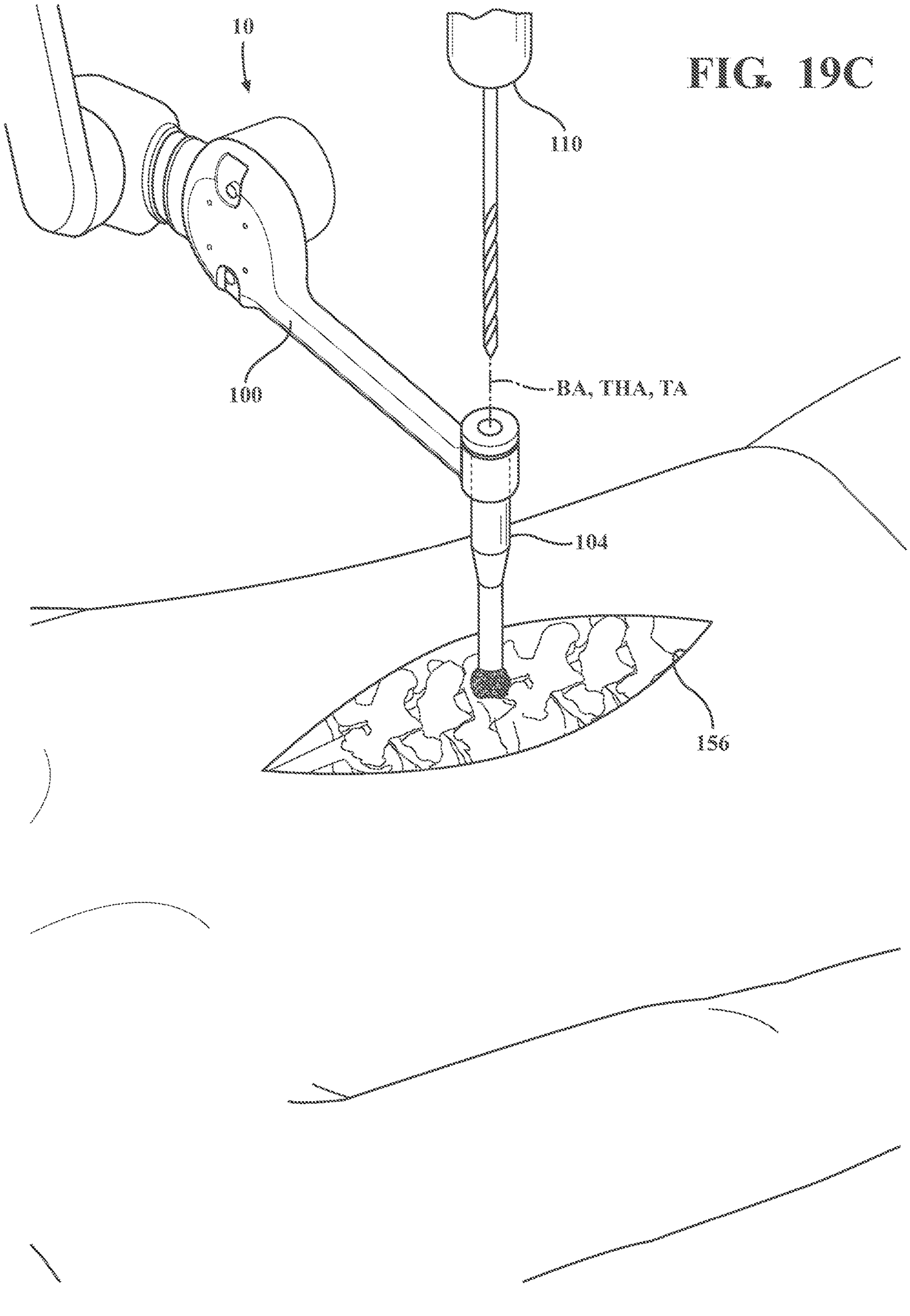
FIG. 19C is a perspective view of the guide tube disposed in the tool holder channel, the outer abrasive surface of the distal portion being engaged with the vertebral body, and the surgical tool disposed above the guide tube with respect to the vertebral body, with the tool holder axis, the target axis, and the body axis being aligned with one another.
Figure 19D:
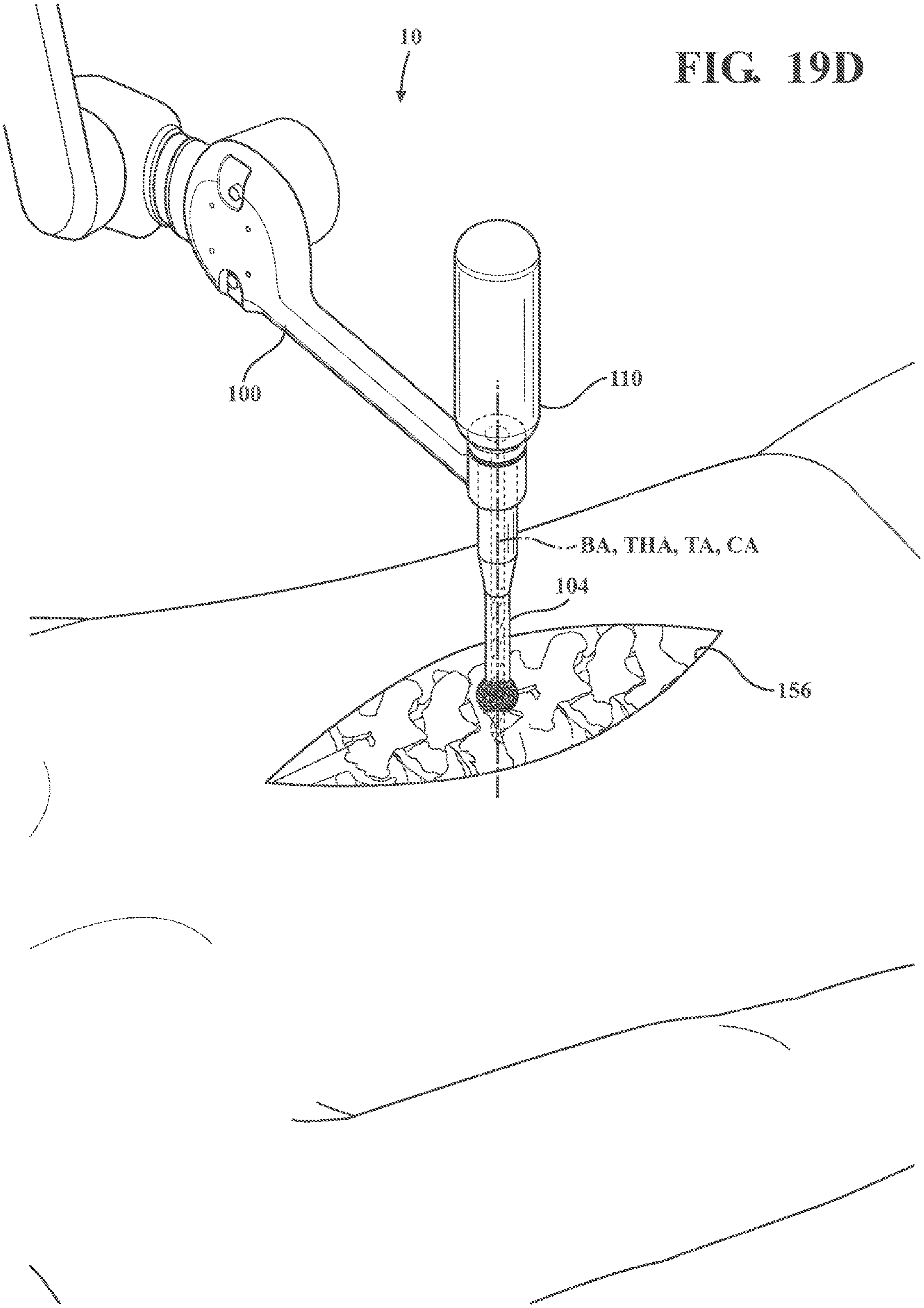
FIG. 19D is a perspective view of the surgical tool being disposed in the body channel of the body of the guide tube, with the tool holder axis, the target axis, the body axis, and a tool axis of the surgical tool being aligned with one another.

FIGS. 19A-19D illustrate an example workflow involving the tool holder 100 and the guide tube 104. The robotic manipulator 14 is configured to align the tool holder 100 such that the tool holder axis THA is able to be aligned with a target axis TA defined relative to the bone, such as a vertebral body, knee, hip, or any other suitable bone of a patient. Specifically, as one example shown in FIG. 19A, the tool holder axis THA and the target axis TA of the vertebral body are misaligned or not yet aligned. In FIG. 19B, the robotic manipulator 14 controls the tool holder 100 such that the tool holder axis THA and the target axis TA are aligned with one another. The guide tube 104 can be disposed in the tool holder channel 102, as shown in FIG. 19C, before or after the axes are aligned. Once the guide tube 104 is disposed on the tool holder channel 102, the side surface 116 of the distal portion 114 is engageable with the vertebral body. When the guide tube 104 is disposed in the tool holder channel 102, the tool holder axis THA, the target axis TA, and the body axis BA may be aligned with one another, as shown in FIG. 19C. Thereafter, the surgical tool 110 may be inserted into the guide tube 104 to enable the surgical tool 110 to engage the vertebral body. After the surgical tool 110 is disposed in the body channel 108 of the body 106 of the guide tube 104, the tool holder axis THA, the target axis TA, the body axis BA, and a tool axis or tool axis CA of the surgical tool 110 may be aligned with one another, as shown in FIG. 19D, which allows the surgical tool 110 to engage the vertebral body in a predetermined location due to the alignment of the tool axis CA with the target axis TA.

The surgical tool 110 is configured to be supported by the guide tube 104 to facilitate the described alignment. In one implementation, the guide tube 104 does not mechanically couple to the surgical tool 110, or vice versa. The surgical tool 110 freely slides within and freely rotates the guide tube 104 while being passively constrained by the body channel 108 of the guide tube 104. In one implementation, the tool holder 100 constrains the guide tube 104 from moving laterally with respect to the tool holder axis THA. However, the guide tube 104 may freely rotate within the tool holder channel 102 about the tool holder axis THA. Additionally, the guide tube 104 may freely axially slide within the tool holder channel 102 along the tool holder axis THA. In other examples, however, the guide tube 104 may be temporarily attached to the surgical tool 110, and both the surgical tool 110 and attached guide tube 104 can be inserted within the tool holder 100. Thereafter, the surgical tool 110 and attached guide tube 104 can be withdrawn from the tool holder 100. Alternatively, the guide tube 104 may be supported by the tool holder 110 but then detached from the surgical tool 110 to enable the surgical tool 110 to be withdrawn from the tool holder 100.

As shown in FIG. 7, the proximal portion 112 may optionally include a proximal flange 118 that has a flange outer diameter D3 greater than the tool holder diameter D1. The proximal flange 118 is configured to be placed above an upper surface 120 of the tool holder 100. Having the proximal flange 118 with a flange outer diameter D3 that is greater than the tool holder diameter D1 prevents the guide tube 104 from sliding entirely out of the tool holder channel 102. This may be useful in situations where only the tool holder 100 supports the guide tube 104. In practice, however, the robotic manipulator 14 may hold the tool holder 100 at position whereby the distal portion 114 of the guide tube 104 engages the bone to provide support for the guide tube 104, but the proximal flange 118 is placed above, and spaced from, the upper surface 120 of the tool holder 100 such that the proximal flange 118 does not contact the upper surface 120 of the tool holder 100. The known measurements (e.g., length) of the guide tube 104 and the tool holder 100 may be stored by the controller 30 to facilitate control of the robotic manipulator 14. By knowing the location of the anatomy from the navigation system 32, the robotic manipulator can be controlled to position the tool holder 100 apart from the anatomy according to a distance that accounts for the known length of the guide tube 104 such that the proximal flange 118 does not contact the upper surface 120 of the tool holder 100.

The distal portion 114 may have a distal outer diameter D4 that is less than or equal to the outer proximal portion diameter D2. As shown in FIGS. 6-9, 11, 13-15, 17, and 18, the distal portion 114 may include a bulbous portion 122 with the bulbous portion 122 having the side surface 116. The bulbous portion 122 may have a curved configuration with respect to the body axis BA, such as a spherical or semispherical configuration. When present, although not required, the bulbous portion 122 may have a bulbous diameter D5 that is greater than the distal outer diameter D4 (as shown in FIG. 6). The bulbous diameter D5 may also be less than or equal to the distal outer diameter D4. The bulbous diameter D5 may be less than or equal to the outer proximal portion diameter D2 or may be greater than the outer proximal portion diameter D2. The bulbous portion 122 is fixed to the body 106.

In one embodiment, the abrasive features 117 of the side surface 116 may be further defined as a plurality of protrusions 124, as particularly shown in FIGS. 6-17. In some implementations, the plurality of protrusions 124 is disposed 360 degrees about the body axis BA. Having the plurality of protrusions 124 disposed 360 degrees about the body axis BA enables the plurality of protrusions 124, regardless of the orientation of the guide tube 104 in the tool holder channel 102, to engage the bone to minimize skiving. Some protrusions 124 may be oriented to face radially outward with respect to the body axis BA to enable the side surface 116 to engage the bone to minimize skiving in a direction perpendicular to the body axis BA. Some protrusions 124 may be oriented to face downward with respect to the body axis BA toward a distal tip 115 of the distal portion 114 to enable the side surface 116 to engage the bone to minimize skiving in a direction normal or parallel to the body axis BA. Some protrusions 124 may be oriented to extend obliquely (upwardly or downwardly) respect to the body axis BA to enable the side surface 116 to engage the bone to minimize skiving in a direction oblique to the body axis BA. Any one or more of the protrusions 124, whether disposed on the side or bottom of the side surface 116, or any location in between, may be configured to engage the bone. Any of the examples of the side surface 116 described herein may be combined and are not solely limited to each implemented shown.

Each protrusion of the plurality of protrusions 124 may have of the same geometry as one another, or the protrusions of the plurality of protrusions 124 may have varying geometries. When the protrusions 124 have varying geometries, the protrusions 124 closer to the distal tip 115 of the distal portion 114 may be larger than the protrusions 124 disposed closer to the proximal portion 112 with respect to the body axis BA.

As shown throughout, any of the protrusions 124 may have a protrusion base 126 and a protrusion tip 128 extending from the protrusion base 126 away from the body axis BA. Said differently, the protrusion base 126 is disposed between the protrusion tip 128 and the body axis BA. Any protrusion 124 may have any number of surfaces that terminate at the protrusion tip 128. The protrusion base 126 may touch an adjacent protrusion base 126.

The plurality of protrusions 124 may have any suitable configuration for engaging the bone of the patient to minimize skiving, such as pyramids, cones, prisms, flanges, wires, prongs, *rhombi*, triangular teeth, and the like. With particular reference to FIG. 8, the protrusions 124 are configured as pyramid protrusions 130. In such implementations, the protrusions 124 may include a first row of pyramids 132 and a second row of pyramids 134 with the first row of pyramids 132 spiraling about the body axis BA and the second row of pyramids 134 spiraling about the body axis BA adjacent the first row of pyramids 132. Alternatively, each pyramid protrusion 130 of the plurality of protrusions 124 may be offset from one another with respect to the body axis BA. It is to be appreciated that any number of rows of pyramid protrusions 130 may be used, such as three, four, five, six, or more rows of pyramids. Furthermore, the pyramid protrusions 130 may be triangular pyramids, square pyramids, rectangular pyramids, pentagonal pyramids, or hexagonal pyramids.

In some implementations, as shown in FIGS. 9-12, the protrusions 124 include flanges 138, such as layers of flanges 138 that may be annular layers, disposed about the body axis BA. The layers of flanges 138 may include a first layer of flanges 150 and a second layer of flanges 152. The layers of flanges 138 may include a third layer of flanges 154, with the second layer of flanges 152 disposed between the first layer of flanges 150 and the third layer of flanges 154 with respect to the body axis BA. The layers of flanges 138 may include any suitable number of layers of flanges, such as four, five, six, or more layers of flanges. In some implementations, at least one layer of the layers of flanges 138 overlaps another layer of the layers of flanges 138 with respect to the body axis BA. For example, the second layer of flanges 152 may overlap the first layer of flanges 150. The layers of flanges 138 may be spaced from one another with respect to the body axis BA.

Figure 10:
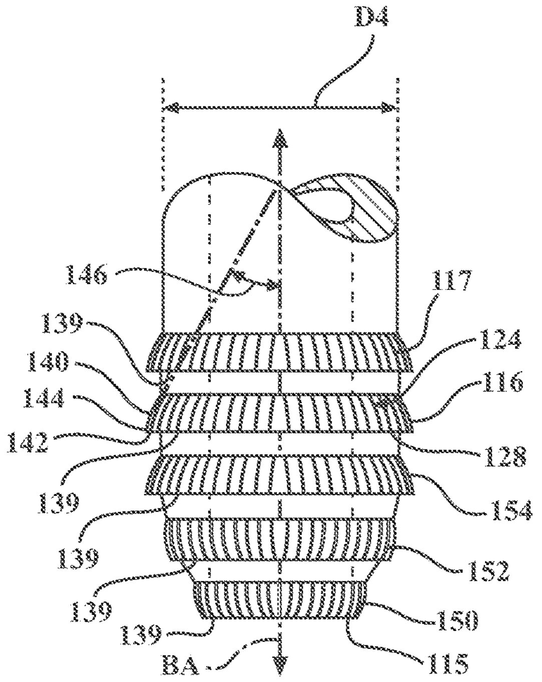
FIG. 10 is a side view of another implementation of the distal portion of the guide tube.

With particular reference to FIGS. 9 and 10, the layers of flanges 138 may have slits 139 cut in the layers of flanges 138. Having slits 139 cut in the layers of flanges results in additional corners defined by the layers of flanges 138, which results in more abrasive points that are configured to engage a bone to minimize skiving.

Each flange 136 includes a first flange surface 140 extending away from the body axis BA and a second flange surface 142 extending away from the body axis BA. The first and second flange surfaces 140, 142 terminate at a flange edge 144. The flange end 144 functions to provide a sharp tip to "hook" the bone to minimize skiving. The first and second flange surfaces 140, 142 may be straight and/or curved. The angle of flange end 144 defined is defined by the first and second flange angles 146, 148. The angle and direction of the flange end 144 may depend on the location of the flange 138 relative to the bulbous portion 122.

The first flange surface 140 is obliquely oriented with respect to the body axis BA, as illustrated in FIGS. 9 and 10. A first flange angle 146 may be defined between the first flange surface 140 and the body axis BA. Depending on its location relative to the bulbous portion 122, the first flange angle 146 may be defined between 0 and +/−90 degrees.

Figure 11:
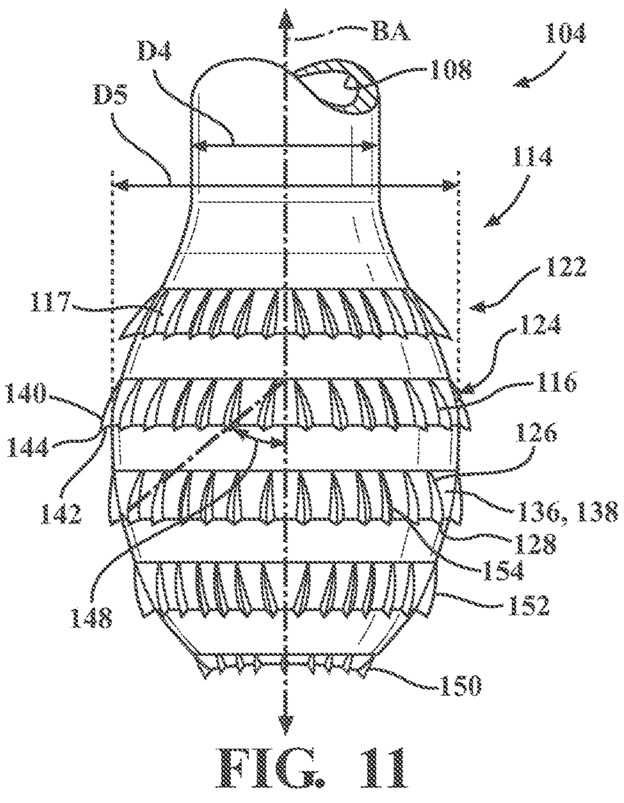
FIG. 11 is a side view of another implementation of the distal portion of the guide tube.
Figure 12:
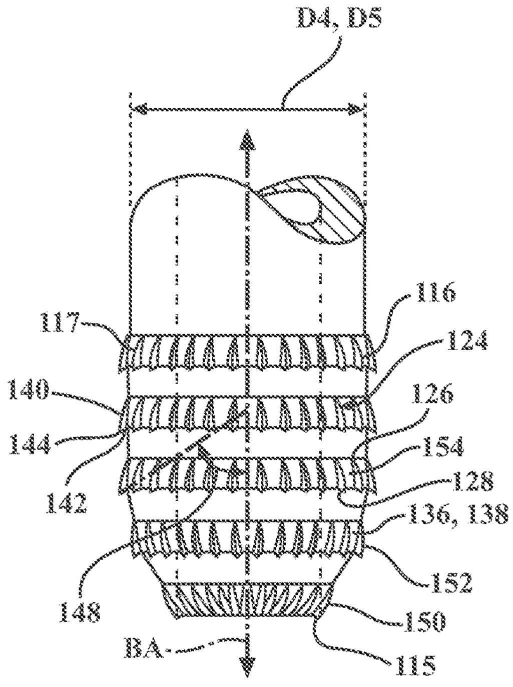
FIG. 12 is a side view of another implementation of the distal portion of the guide tube.

The second flange surface 142 may be perpendicularly oriented with respect to the body axis BA, as shown in FIGS. 9 and 10. Additionally, or alternatively, some or all of the second flange surfaces 142 may be obliquely oriented with respect to the body axis BA, as shown in FIGS. 11 and 12. A second flange angle 148 may be defined between the second flange surface 142 and the body axis BA. If the second flange surface 142 is perpendicularly oriented with respect to the body axis BA, the second flange angle 148 will be substantially 90 degrees. If the second flange surface 142 is obliquely oriented with respect to the body axis BA, the second flange angle 148 may be defined between 0 and +/−90 degrees, depending on its location relative to the bulbous portion 122. In one implementation, the first and second flange surfaces 140, 142 may be corresponding to one another such that the first and second flange angles 146, 148 may be substantially similar. For example, the first and second flange surfaces 140, 142 may be co-planar and opposite sides of a curved flange or planar flange. In such examples, the flange edge 144 may have the same thickness as the body of the flange 138. The angle of flange end 144 may be defined between 0 and +/−90 degrees.

As described above, the side surface 116 implemented by protrusions 124 defined by wires or prongs extending from the bulbous portion 122. The prongs may extend radially from a center of the bulbous portion 122. This way, the prongs can engage the bone from any direction to prevent skiving. Any number of prongs may extend from the bulbous portion 122. The prongs may be spaced apart from each other by any suitable distance, e.g., 1 mm or less. The prongs may be blunt tipped or sharp tipped. The length of the prongs may relatively short, e.g., 1-2 mm to provide a predictable contact with the bone. The prongs may be stiff or flexible, or any combination thereof.

Figure 13:
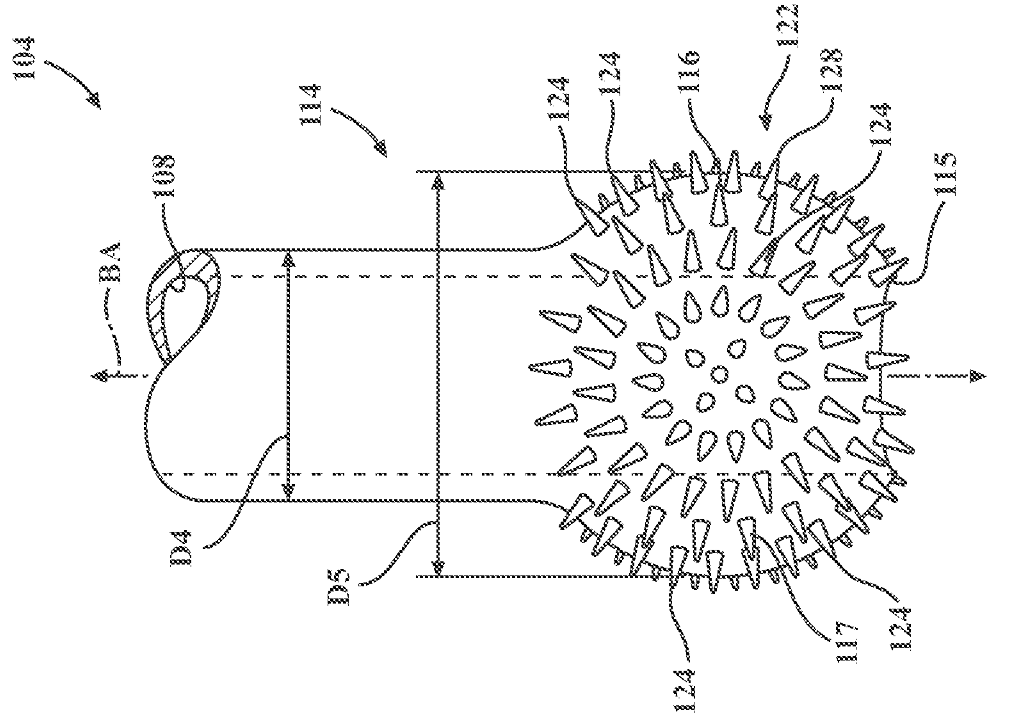
FIG. 13 is a side view of another implementation of the distal portion of the guide tube.

FIG. 13 illustrates the side surface 116 implemented by protrusions 124 defined by cones extending from the bulbous portion 122. The cones may extend radially from a center of the bulbous portion 122. This way, the cones can engage the bone from any direction to prevent skiving. Any number of cones may extend from the bulbous portion 122. The cones may be spaced apart from each other by any suitable distance, e.g., 1 mm or less. The cones may be blunt tipped or sharp tipped. The length of the cones may relatively short, e.g., 1-2 mm or 1 mm or less to provide a predictable contact with the bone. The cones may be stiff or flexible, or any combination thereof.

Figure 14:
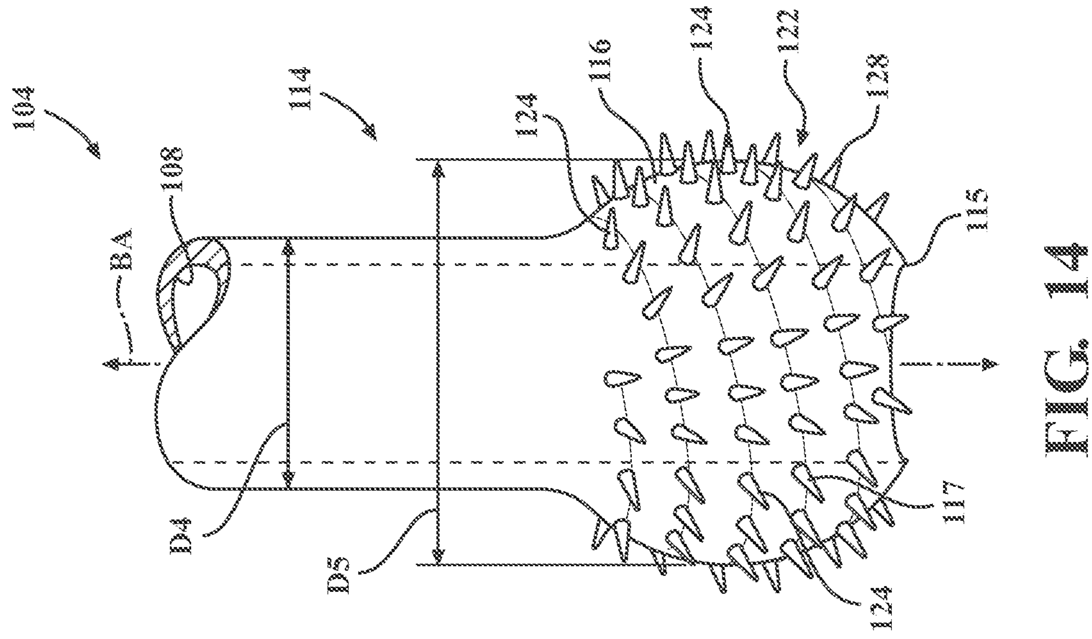
FIG. 14 is a side view of another implementation of the distal portion of the guide tube.
Figure 15:
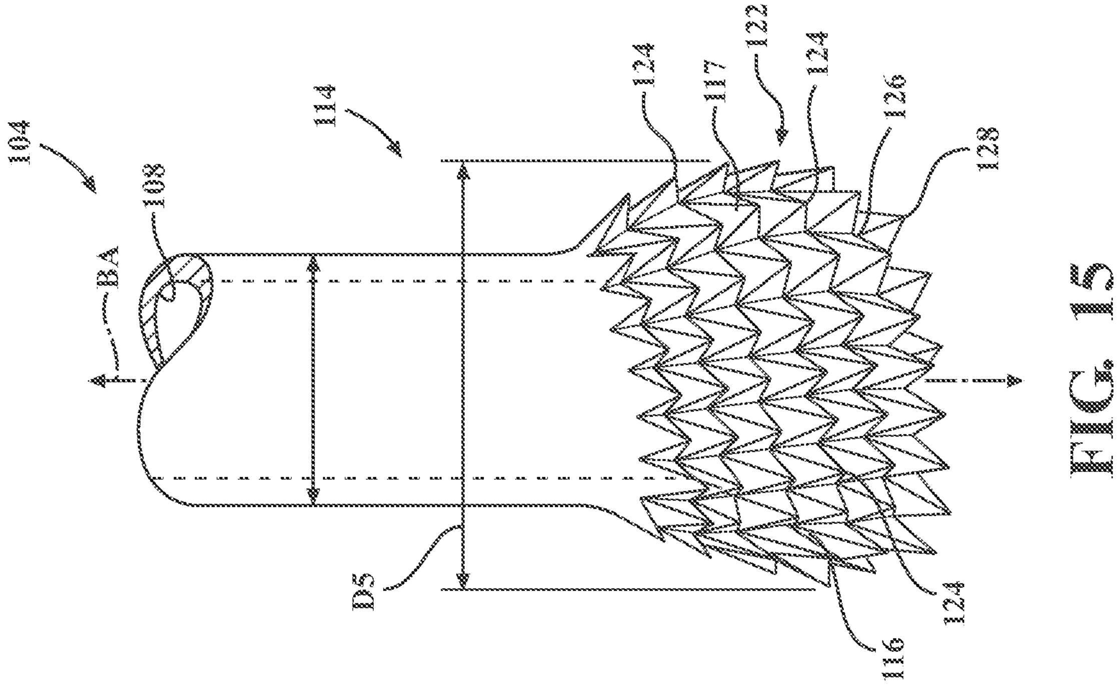
FIG. 15 is a side view of another implementation of the distal portion of the guide tube.

FIGS. 14 and 15 illustrates the side surface 116 implemented by protrusions 124 having a helical configuration with respect to the body axis BA. Although the protrusions 124 are shown as cones in FIG. 14 and triangular teeth in FIG. 15, it is to be appreciated that any other suitable protrusion configuration, such as pyramids, cones, prisms, flanges, wires, prongs, *rhombi*, and the like, may have a helical configuration with respect to the body axis BA. The protrusions 124 having a helical configuration with respect to the body axis BA helps the distal portion 114 of the body 106 of the guide tube 104 to insert into the patient. In particular, the helical configuration of the protrusions 114 with respect to the body axis BA helps rotate the guide tube 104 and insert through softer tissue (i.e., not bone) of the patient. Once the distal portion 114 of the body 106 of the guide tube 104 is inserted into the patient, the protrusions 114 then are able to engage the bone to minimize skiving.

Figure 16:
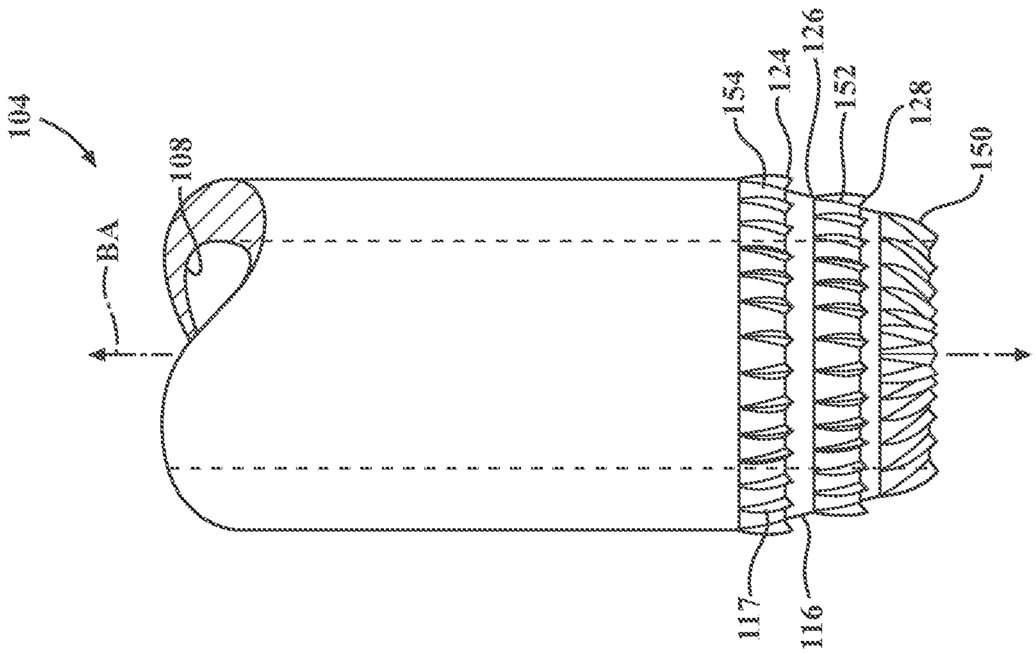
FIG. 16 is a side view of another implementation of the distal portion of the guide tube.

FIG. 16 illustrates the side surface 116 implemented by rows of protrusions 116 disposed about the body axis BA. Although the rows of protrusions 116 are illustrated as being triangular teeth in FIG. 16, it is to be appreciated that the protrusions 116 may have any other suitable configuration, such as pyramids, cones, prisms, flanges, wires, prongs, *rhombi*, and the like, and include rows disposed about the body axis BA.

Figure 17:
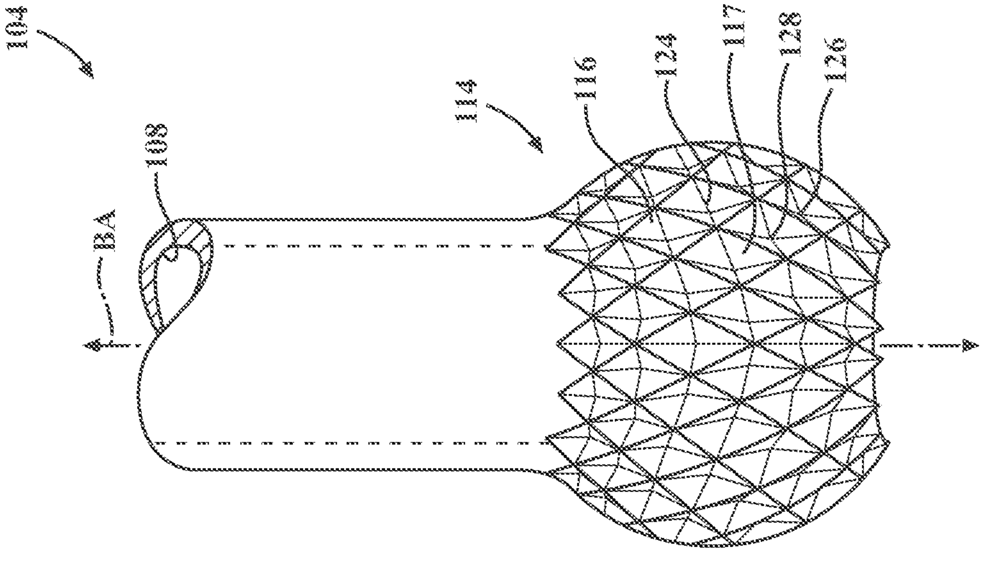
FIG. 17 is a side view of another implementation of the distal portion of the guide tube.

FIG. 17 illustrates the side surface 116 implemented by protrusions 124 having a diamond-shaped configuration, and optionally may have the protrusion base 126 and a protrusion tip 128. As shown in FIG. 17, the protrusions 124 may have a helical configuration with respect to the body axis BA.

Figure 18:
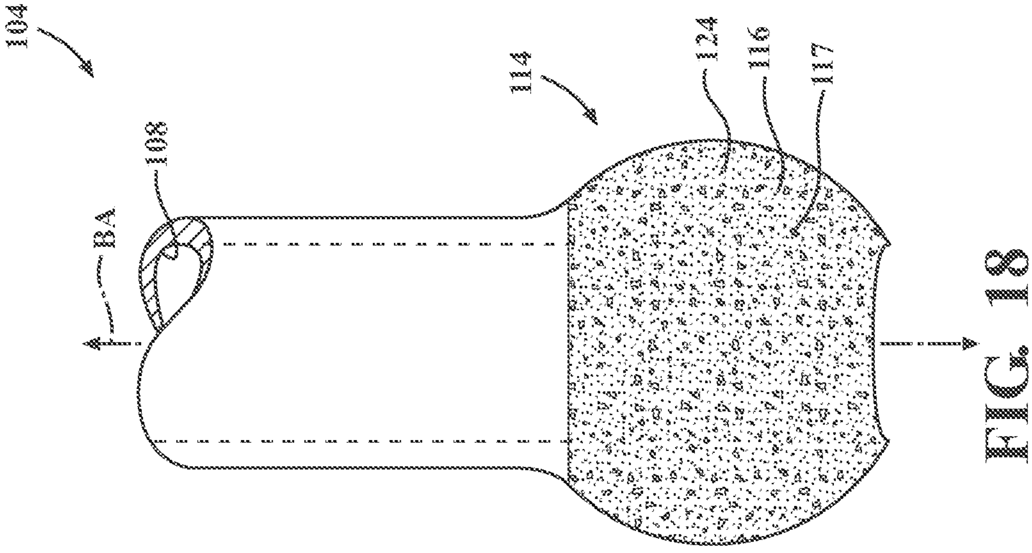
FIG. 18 is a side view of another implementation of the distal portion of the guide tube.

FIG. 18 illustrates the side surface 116 implemented by protrusions 124 formed as an abrasive coating. The abrasive coating may include diamonds, abrasive features, protrusions, or any other suitable materials or configurations for preventing skiving.

Figure 20:
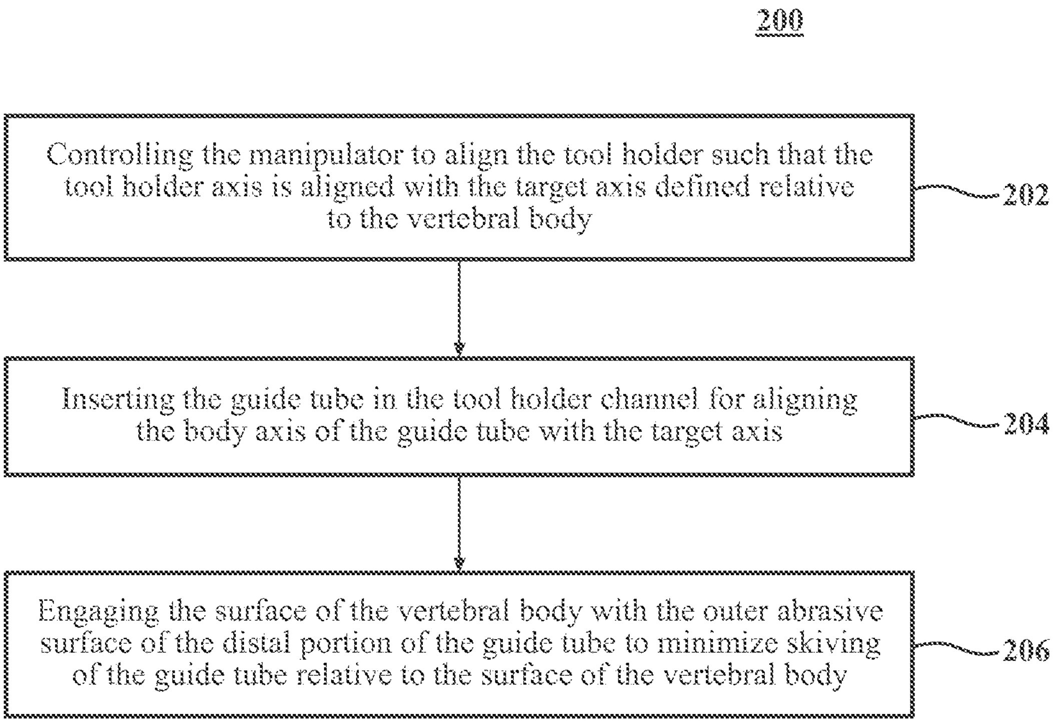
FIG. 20 is a flowchart of a method of operating the surgical system, according to one implementation.

FIG. 20 illustrates steps of an example method 200 of operating the system 10 to facilitate a spinal procedure on the vertebral body. The method 200 includes the step 202 of controlling the manipulator 14 to align the tool holder 100 such that the tool holder axis THA is aligned with the target axis TA defined relative to the vertebral body, as shown when progressing from FIG. 19A to FIG. 19B. The method 200 also includes the step 204 of inserting the guide tube 104 in the tool holder 100 for aligning the body axis BA of the guide tube 104 with the target axis TA, as also shown in FIG. 19C. The method 200 further includes the step 206 of engaging the surface of the vertebral body with the side surface 116 of the distal portion 114 to minimize skiving of the guide tube 104 relative to the surface of the vertebral body, as also shown in FIG. 19C.

The method 200 may optionally include, after step 202, the step of inserting the guide tube 104 through a patient incision 156 until the side surface 116 of the distal portion 114 engages the surface of the vertebral body. The method 200 may include, after engaging the surface of the vertebral body with the side surface 116 of the distal portion 114, inserting the surgical tool 110 in the body channel 108 of the guide tube 104, as shown in FIG. 19D.

The described guide tube 104 provides improved features to facilitate engagement between the guide tube 104 and the complex surface of the target vertebra. The guide tube 104 reduces inaccuracies in surgical workflows by reducing the potential of skiving. The side surface 116 provides anti-skiving capability from downward, oblique, and sideways directions relative to the bone surface. Hence, the side surface 116 facilitates robust engagement with bone surface from any practical angle of insertion and provides flexibility when encountering complex contours of the surface. The guide tube 104 provides predictable and accurate engagement relative to the bone surface, which results in improved accuracy in alignment of the guide tube 104 and surgical tools inserted therein relative to the target trajectory. Other advantages, other than those described herein, are readily understood in view of the detailed description and figures.

Several implementations have been discussed in the foregoing description. However, the implementations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described. The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical system to facilitate a spinal procedure on a vertebral body, the surgical system comprising:

a robotic manipulator comprising an arm and a tool holder coupled to the arm, wherein the tool holder defines a tool holder channel extending along a tool holder axis, and wherein the tool holder channel has a tool holder diameter; and a guide tube configured to slide into the tool holder channel and comprising:

a body extending along a body axis and defining a body channel that is configured to receive a surgical tool, wherein the body has a proximal portion defining the body channel and having an outer proximal portion diameter that is less than or equal to the tool holder diameter such that the proximal portion is slidable into the tool holder channel to align the body with the tool holder, and wherein the body has a distal portion extending from the proximal portion along the body axis and further defining the body channel, wherein the distal portion has a distal outer diameter and comprises a bulbous portion having a bulbous diameter greater than the distal outer diameter, the bulbous portion comprising a side surface disposed about the body axis, and wherein the side surface comprises abrasive features extending away from the body axis and configured to engage a surface of the vertebral body to minimize skiving.

2. The surgical system of claim 1, wherein the robotic manipulator is configured to align the tool holder such that the tool holder axis is aligned with a target axis defined relative to the vertebral body, and wherein the body axis of the guide tube is aligned with the target axis when the guide tube is inserted into the tool holder channel.

3. The surgical system of claim 1, wherein the guide tube is configured to be passively supported by the tool holder.

4. The surgical system of claim 3, wherein the guide tube is freely slidable along the tool holder axis.

5. The surgical system of claim 1, wherein the proximal portion has a proximal flange having a flange outer diameter greater than the tool holder diameter, and wherein the proximal flange is configured to be placed above an upper surface of the tool holder.

6. The surgical system of claim 1, wherein the abrasive features of the side surface are further defined as a plurality of protrusions.

7. The surgical system of claim 6, wherein at least a portion of the plurality of protrusions are oriented to face downward with respect to the body axis toward a distal end of the distal portion.

8. The surgical system of claim 1, wherein the guide tube is configured to mechanically couple to the tool holder.

9. The surgical system of claim 1, wherein the bulbous diameter is less than or equal to the tool holder diameter.

10. A guide tube of a surgical system, the surgical system being configured to facilitate spinal procedure on a vertebral body and the surgical system including a robotic manipulator including an arm and a tool holder coupled to the arm, the tool holder defining a tool holder channel extending along a tool holder axis, and the tool holder channel having a tool holder diameter, the guide tube comprising:

a body extending along a body axis and defining a body channel that is configured to receive a surgical tool, wherein the body has a proximal portion defining the body channel and having an outer proximal portion diameter that is configured to be less than or equal to the tool holder diameter such that the proximal portion is configured to be slidable into the tool holder channel to align the body with the tool holder, and wherein the body has a distal portion extending from the proximal portion along the body axis and further defining the body channel;

wherein the distal portion has a distal outer diameter and comprises a bulbous portion having a bulbous diameter greater than the distal outer diameter, the bulbous portion comprising a side surface disposed about the body axis, and wherein the side surface comprises abrasive features extending away from the body axis and configured to engage a surface of the vertebral body to minimize skiving.

11. The guide tube of claim 10, wherein the abrasive features of the side surface are disposed 360 degrees about the body axis.

12. The guide tube of claim 10, wherein the abrasive features of the side surface are further defined as a plurality of protrusions, and wherein at least a portion of the plurality of protrusions are oriented to face downward with respect to the body axis toward a distal end of the distal portion.

13. The guide tube of claim 12, wherein each protrusion of the plurality of protrusions is of the same geometry.

14. The guide tube of claim 12, wherein the protrusions of the plurality of protrusions have varying geometries.

15. The guide tube of claim 12, wherein a geometry of at least one protrusion is a prism.

16. The guide tube of claim 12, wherein a geometry of at least one protrusion is a cone.

17. The guide tube of claim 12, wherein a geometry of at least one protrusion is a prong.

18. The guide tube of claim 12, wherein each protrusion has a protrusion base and a protrusion tip extending from the protrusion base away from the body axis.

19. The guide tube of claim 12, wherein the plurality of protrusions has a helical configuration with respect to the body axis.

20. The guide tube of claim 12, wherein the plurality of protrusions comprises layers of flanges disposed annularly about the body axis.

21. The guide tube of claim 20, wherein each flange of the layers of flanges comprises a first flange surface extending away from the body axis and a second flange surface extending away from the body axis, and wherein the first and second flange surfaces terminate at a flange edge that is configured to engage the vertebral body to minimize skiving.

22. The guide tube of claim 21, wherein the first flange surface is obliquely oriented with respect to the body axis.

23. The guide tube of claim 10, wherein the proximal portion has a proximal flange having a flange outer diameter configured to be greater than the tool holder diameter such that the proximal flange is configured to be placed above an upper surface of the tool holder, wherein the distal outer diameter is less than the flange outer diameter.

24. The guide tube of claim 10, wherein the bulbous diameter is less than or equal to the tool holder diameter.

25. A method of operating a surgical system to facilitate spinal procedure on a vertebral body, the surgical system including a robotic manipulator comprising an arm and a tool holder coupled to the arm, wherein the tool holder defines a tool holder channel extending along a tool holder axis and the tool holder channel defining a tool holder diameter; a guide tube including a body extending along a body axis and defining a body channel that is configured to receive a surgical tool, wherein the body has a proximal portion defining the body channel and having an outer proximal portion diameter that is less than or equal to the tool holder diameter, and the body has a distal portion extending from the proximal portion along the body axis and further defining the body channel, and wherein the distal portion of the body has a distal outer diameter and includes a bulbous portion having a bulbous diameter greater than the distal outer diameter, the bulbous portion including a side surface disposed about the body axis and comprising abrasive features extending away from the body axis, the method comprising the steps of:

controlling the robotic manipulator to align the tool holder such that the tool holder axis is aligned with a target axis defined relative to the vertebral body;

inserting the guide tube in the tool holder for aligning the body axis of the guide tube with the target axis; and engaging the surface of the vertebral body with the side surface of the bulbous portion to minimize skiving of the guide tube relative to the surface of the vertebral body.

26. The method of claim 25, further comprising, after controlling the robotic manipulator to align the tool holder such that the tool holder axis is aligned with the target axis, inserting the guide tube through a patient incision until the side surface of the bulbous portion engages the surface of the vertebral body.

27. The method of claim 26, further comprising, after engaging the surface of the vertebral body with the side surface of the bulbous portion, inserting the surgical tool in the body channel of the guide tube.

28. The method of claim 25, wherein engaging the surface of the vertebral body comprises passively engaging the surface with the side surface of the bulbous portion.

29. A surgical system comprising:

a robotic manipulator comprising an arm and a tool holder coupled to the arm, wherein the tool holder defines a tool holder channel;

a surgical tool; and a guide tube configured to freely slide relative to the tool holder channel and being separated from the surgical tool, the guide tube comprising a body defining a channel along a body axis that is configured to receive the surgical tool therethrough such that the surgical tool is configured to freely slide relative to the guide tube, wherein the body has a distal portion having a distal outer diameter and comprising a bulbous portion having a bulbous diameter greater than the distal outer diameter, the bulbous portion comprising a side surface disposed about the body axis, and wherein the side surface comprises abrasive features extending away from the body axis.

* * * * *